United States Patent
Fujimaru et al.

(10) Patent No.: US 7,196,139 B2
(45) Date of Patent: Mar. 27, 2007

(54) WATER-ABSORBENT RESIN COMPOSITION

(75) Inventors: Hirotama Fujimaru, Himeji (JP); Katsuyuki Wada, Himeji (JP); Kunihiko Ishizaki, Suita (JP); Motohiro Imura, Nara (JP); Hiroki Inoue, Kyoto (JP)

(73) Assignee: Nippon Shokubai Co., Ltd., Osaka (JP)

(*) Notice: Subject to any disclaimer, the term of this patent is extended or adjusted under 35 U.S.C. 154(b) by 378 days.

(21) Appl. No.: 10/746,873

(22) Filed: Dec. 24, 2003

(65) Prior Publication Data
US 2004/0254553 A1 Dec. 16, 2004

(30) Foreign Application Priority Data
Dec. 26, 2002 (JP) ............................ 2002-376785

(51) Int. Cl.
C08J 3/03 (2006.01)
C08L 33/02 (2006.01)

(52) U.S. Cl. ................. 525/218; 525/221; 524/522; 524/916

(58) Field of Classification Search ........... 525/218, 525/221, 522, 916; 524/522, 916
See application file for complete search history.

(56) References Cited

U.S. PATENT DOCUMENTS

| | | | |
|---|---|---|---|
| 4,093,776 A | 6/1978 | Aoki et al. | |
| 4,286,082 A | 8/1981 | Tsubakimoto et al. | |
| 4,340,706 A | 7/1982 | Obayashi et al. | |
| 4,367,323 A | 1/1983 | Kitamura et al. | |
| 4,446,261 A | 5/1984 | Yamasaki et al. | |
| 4,625,001 A | 11/1986 | Tsubakimoto et al. | |
| 4,683,274 A | 7/1987 | Nakamura et al. | |
| 4,873,299 A | 10/1989 | Nowakowsky et al. | |
| 4,973,632 A | 11/1990 | Nagasuna et al. | |
| 4,985,518 A | 1/1991 | Alexander et al. | |
| 5,112,902 A * | 5/1992 | Moriya et al. ............. | 524/503 |
| 5,124,416 A | 6/1992 | Haruna et al. | |
| 5,244,735 A | 9/1993 | Kimura et al. | |
| 5,250,640 A | 10/1993 | Irie et al. | |
| 5,264,495 A | 11/1993 | Irie et al. | |
| 5,346,986 A | 9/1994 | Schneider et al. | |
| 5,380,808 A | 1/1995 | Sumiya et al. | |
| 6,103,785 A | 8/2000 | Kajikawa et al. | |
| 6,156,678 A | 12/2000 | Mukaida et al. | |
| 6,258,996 B1 * | 7/2001 | Goldman ................. | 604/368 |
| 6,444,744 B1 | 9/2002 | Fujimaru et al. ......... | 524/556 |
| 6,458,896 B1 | 10/2002 | Collette et al. | |
| 6,562,879 B1 | 5/2003 | Hatsuda et al. | |
| 2003/0208174 A1 | 11/2003 | Minato et al. | |

FOREIGN PATENT DOCUMENTS

| | | |
|---|---|---|
| EP | 0 811 636 | 12/1987 |
| EP | 0 695 762 | 7/1996 |
| EP | 0 922 717 | 9/1999 |
| EP | 0 955 086 | 11/1999 |
| JP | 56-93716 | 7/1981 |
| JP | 56-131608 | 10/1981 |
| JP | 57-158209 | 9/1982 |
| JP | 61-115904 | 3/1986 |
| JP | 61-157513 | 7/1986 |
| JP | 61-231003 | 10/1986 |
| JP | 61-231004 | 10/1986 |
| JP | 62-95307 | 5/1987 |
| JP | 6-505037 | 6/1994 |
| JP | 2574032 | 10/1996 |
| JP | 11-28355 | 2/1999 |
| JP | 11-130968 | 5/1999 |
| JP | 11-333292 | 7/1999 |
| JP | 11-246625 | 9/1999 |
| JP | 11-279207 | 10/1999 |
| JP | 2000-15093 | 1/2000 |
| JP | 2000-302876 | 10/2000 |
| JP | 2000-513392 | 10/2000 |
| JP | 2000-354760 | 12/2000 |
| JP | 2003-33970 | 11/2003 |
| WO | WO92/13912 | 8/1992 |
| WO | WO94-20543 | 9/1994 |

\* cited by examiner

*Primary Examiner*—James J. Seidleck
*Assistant Examiner*—Olga Asinousky
(74) *Attorney, Agent, or Firm*—Fish & Richardson P.C.

(57) ABSTRACT

A water-absorbent resin composition excelling in an absorption capacity under pressure, a first transition of initial absorption, and the small amount of rewet is provided. It comprises a water-absorbent resin obtained by aqueous solution polymerization and by reversed-phase suspension or reversed-phase emulsion polymerization and shows a CSF of not less than 20 g/g or an AAP of not less than 20 g/g or an SFC of not less than 10 (unit: $10^{-7} \times cm^3 \times s \times g^{-1}$). The gaps among resin particles owing to the difference in shape form optimum gap widths for the sake of capillarity. The resin composition consequently formed, therefore, manifests such excellent properties without the influences of a surfactant or an emulsifier.

30 Claims, 10 Drawing Sheets

WATER-ABSORBENT RESIN COMPOSITION

BACKGROUND OF THE INVENTION

1. Field of the Invention

This invention relates to a water-absorbent resin composition which is a mixture of a plurality of water-absorbent resins differing in form and obtained by different methods of polymerization and which excels in absorption characteristics such as an absorption capacity, permeability (flow conductivity of physiological saline), a capillary absorption capacity, the first transition of initial absorption, and the decrease in an amount of rewet of absorbed fluid.

2. Description of the Related Art

Water-absorbent resins capable of absorbing water to tens to hundreds of times their own weights have been developed and have been used for absorption and retention of water such as, first of all, in the field of sanitary materials including sanitary goods and disposable diapers, the field of agricultural and horticulture materials, the field of foodstuffs demanding preservation of freshness, and the industrial fields specializing in prevention of dew formation and heat insulation. As such water-absorbent resins, the hydrolyzate of starch-acrylonitrile graft copolymer, the product of neutralization of starch-acrylic acid graft polymer, the product of saponification of vinyl acetate-acrylic ester copolymer, the hydrolyzate of acrylonitrile copolymer or the product of cross-linkage thereof, cross-linked polymers such as polyethylene imine cross-linked polymer and polyallyl amine cross-linked polymer, and the cross-linked polymer of partially neutralized polyacrylic acid salt have been known.

The water-absorbent resin is requested the quality thereof depending on the purpose for which it is used. The characteristic quality which the water-absorbent resin is intended for such a sanitary material as disposable diaper, for example, is required to manifest resides in attaining a high absorption capacity with an aqueous liquid under a high pressure. For this purpose is available a technique which comprises causing molecular chains in the proximity of the surface of the water-absorbent resin to cross-link thereby increasing the crosslink density of the surface layer, securing among the particles such voids as allow the liquid to migrate when the polymer absorbs water and swells, thereby preventing the absorption capacity of the water-absorbent resin from degrading even when the resin is exposed to high pressure. Since the size of a surface area generally contradicts the absorption capacity under pressure, an increase of the surface area of particles of the polymer results in rendering uniform surface cross-linkage of the polymer proportionately difficult because it renders uniform incorporation of a cross-linking agent in the polymer proportionately difficult. To cope with these difficulties, methods of cross-linking treatment to the neighborhood of surface of a surface porous sodium acrylate polymer to a cross-linking treatment (the official gazette of International Publication No. 94/20543, the official gazette of International Unexamined Patent Publication No. 06-505037, and the specification of European Patent No. 0695762) are conceivable. Even in these methods, when the surface cross-link density is heightened to increase the absorption capacity under pressure during the cross-linking treatment of the neighborhood of surface of the porous polymer, the hydrophilicity of the surface is degraded because it is difficult for the porous polymer to control of the cross-link density. In spite of the use of the porous polymer, therefore, such problems as lowering the speed of water absorption have persisted.

A technique for mixing a plurality of water-absorbent resins differing inproperties thereby improving properties of a water-absorbent resin. For example, a water absorbing agent having peaks of particle-size distributions in 1000–500 μm and 750–250 μm has been disclosed (the official gazette of JP-A-11-28355). Since the mixture of coarse particles and fine particles are endowed a proper discontinuous arrangement by gaps of particles having suitable particle-size interval, it said that an absorbent article which satisfied both quick diffusion in the lateral direction and quick absorption in the vertical direction was able to be obtained. A water-absorbent resin in a powdery state, possesses a normal standard deviation of not less than 130 in particle-size distribution, and preferably forms not less than two peaks in the particle-size distribution (official gazette of JP-A-11-246625). For the purpose of obtaining a powdery water-absorbent resin having two or more mutually different average particle sizes, this invention contemplates classifying a water-absorbent resin and then mixing not less than two kinds of water-absorbent resins obtained by the classification and possessing no mutually overlapping ranges of particle size. Also, a water absorbing agent formed by fixing on the surface of water-absorbent resin particles fine water absorptive particles having a lower absorption capacity than the absorption capacity of the water-absorbent resin particles is disclosed (official gazette of JP-A-11-333292). Further, a water-absorbing agent which is obtained by mixing a water-absorbent resin (A1) capable of absorbing physiological saline in a volume of not less than 55 g/g under no load and absorption speed of not less than 40 sec a water-absorbent resin (A2) capable of absorbing physiological saline in a volume of not less than 20 g/g under a load of 40 g/cm$^2$ and possessing a coefficient of gel elasticity of not less than 750 N/m$^2$ at a mixing ratio of (A1):(A2) in the range of (3:7)–(7:3) by weight and which is preferable for absorbing articles is disclosed (official gazette of JP-A-2000-15093). Incidentally, the official gazettes of JP-A-11-28355, JP-A-11-246625, JP-A-11-333292, and JP-A-2000-15093 demonstrate in working examples mixed use of water-absorbent resins obtained by aqueous solution polymerization.

A granular water-absorbent resin characterized produced by binding beads of water-absorbent resin having not less than two frequency distributions and having a ratio of smaller median particle diameters to the largest median particle diameter in the range of 1/3000–1/1.5 and having an average particle diameter in the range of 200–10000 μm is disclosed (official gazette of JP-A-11-130968). The granular water-absorbent resin is obtained by varying the speed of agitation halfway in the course of the reversed phase suspension polymerization.

An absorbent article using a water-absorbent resin of a fast absorption speed and a water-absorbent resin of a slow absorption speed at a ratio in the range of 90/10–10/90 and having an absorbent resin concentration of not less than 80 wt. % is disclosed (official gazette of JP-A-2000-354760). The exaltation of the ability of capillary absorption by combining two super-absorptive powders is also disclosed (official gazette of International Unexamined Patent Publication No. 2000-513392).

The water-absorbent resins in the inventions of the official gazettes of JP-A-11-28355, JP-A-11-246625, JP-A-11-333292, and JP-A-2000-15093 are irregular-shape polymers obtained by crushing polymers polymerized in an aqueous solution. They, therefore, have comparatively low bulk densities and prove unfavorable for the purpose of enabling them to form an absorbing article in a small thickness or allowing them to transport in a compact size. The water-absorbent resins which are used in the invention of the official gazette of JP-A-11-130968 and the official gazette of International Unexamined Patent Publication No. 2000-513392 are obtained by the reverse phase suspension polymerization and are in the form of spheres or an aggregate thereof and, therefore, entail the problem that the water-absorbent resin particles will readily fall down from the absorbent articles during the formation thereof since a bulk specific gravity thereof is relatively high as 0.9 g/ml. The water-absorbent resin obtained by the reverse phase suspension or emulsion polymerization entails the problem of suffering the surface tension of an absorbing liquid such as urine to lower owing to the use of a surfactant or an emulsifier during the production of the resin and consequently suffering the resin, when used as an absorbent article, to increase the amount of rewet of the solution once absorbed, though the mechanism of the rewet(wet back) remains yet to be elucidated in detail.

The term "ability of capillary absorption" mentioned in the official gazette of International Unexamined Patent Publication No. 2000-513392 refers to absorption capacity under pressure and differs completely from capillary suction force in the present invention. As described in detail in the subsequent paragraph, this magnitude is measured by the use of a device illustrated diagrammatically in FIG. 1. Specifically, this measurement is attained by placing a given sample (water-absorbent resin) at a position several tens of cm higher than the level of physiological saline held in a solution vessel and determining the ability of the sample to absorb the saline by capillary against the negative pressure of the water column of the height mentioned above. Heretofore, examples of measuring the ability of absorption of a sample placed in the absence of negative pressure, namely at a position equal to the level of a solution held in a reservoir have been observed (WO88/01282). No example of any water-absorbent resin measured for ability of capillary absorption under such negative pressure has existed up to date. The correlation between the ability of capillary absorption manifested by the water-absorbent resin used in the method of this invention and the mixture of water-absorbent resins has never been known in the art.

The disposable diaper forms one of the practical uses which are found for the water-absorbent resin. Since the baby wearing the disposable diaper moves around incessantly, the load exerted to bear on the water-absorbent resin is not fixed. Even when the water-absorbent resin exhibits a high absorption capacity under a high load, where are times when the ability of the resin to absorb water relative to the pressure is not fixed. Only because the water-absorbent resin exhibits a high absorption capacity under high pressure, namely the load at most in the range of 10—several tens of g/cm$^2$ estimated from the ordinary body weight (in the neighborhood of 10 kg) of a baby, it does not necessarily follow that the resin, when incorporated in an actual disposable diaper, will function fully satisfactorily. The fact that the resin possesses a high ability to absorb water in the absence of the application of pressure and a ability to effect capillary absorption of water under negative pressure and the resin entails only a small amount of rewet are very important factors. When the absorption capacity under pressure is heightened, the absorption capacity under no pressure is lowered because of an increase in the surface crosslink density, with the result that well-balanced absorption properties will not be easily obtained and the absorbent article will not be fully improved in solid state properties.

SUMMARY OF THE INVENTION

The present inventor has made an elaborate study on differences in methods employed for polymerizing water-absorbent resins and average particle diameters of the resins consequently produced and has consequently found that by combining an irregular sharp water-absorbent resin and a spherical or pelletized water-absorbent resin and mixing the water-absorbent resins different in form, specifically by mixing a water-absorbent resin obtained by aqueous solution polymerization and a water-absorbent resin obtained by reversed-phase suspension or emulsion polymerization and formulating the mixture so as to satisfy any of the conditions that the capillary suction force of the mixture under the gradient of negative pressure is not less than 20 g/g, that the absorption capacity under pressure is not less than 20 g/g, and that a flow conductivity of physiological saline is not less than $10 \times 10^{-7}$ cm$^3$·s/g, it is made possible to obtain a water-absorbent resin composition which manifests the ability to effect capillary absorption, the absorption capacity under pressure, and the dispersion of a solution during the absorption of urine, for example, to well-balanced degrees and which possesses very high absorption properties. This invention has been perfected as a result. When this water-absorbent resin composition is used in such an absorbent article as disposable diaper, in spite of the use of a water-absorbent resin obtained by the reversed-phase suspension or emulsion polymerization, it can realize the repression of the effect of a surfactant or an emulsifier in exalting the amount of rewet and the exaltation of the power of capillary absorption. Since the bulk specific density is heightened at the same time, this resin composition, when used as an absorbent article, easily permit it to be compacted and decreased in wall thickness and to be transported and stored in a compact form.

According to this invention, owing to the use of a mixture of water-absorbent resins obtained by different methods of polymerization, it is made possible to obtain a water-absorbent resin composition which excels in the absorption capacity under pressure, the capillary suction force under negative pressure, the flow conductivity of physiological saline, and the first transition of the initial absorption, exhibits well-balanced absorption properties, and entails only a small amount of rewet. It particularly manifests a conspicuous effect in lowering the amount of rewet which has never been attained by a conventional water-absorbent resin composition using a water-absorbent resin obtained by reverse-phase suspension or emulsion polymerization.

DESCRIPTION OF THE PREFERRED EMBODIMENTS

Figure 1:
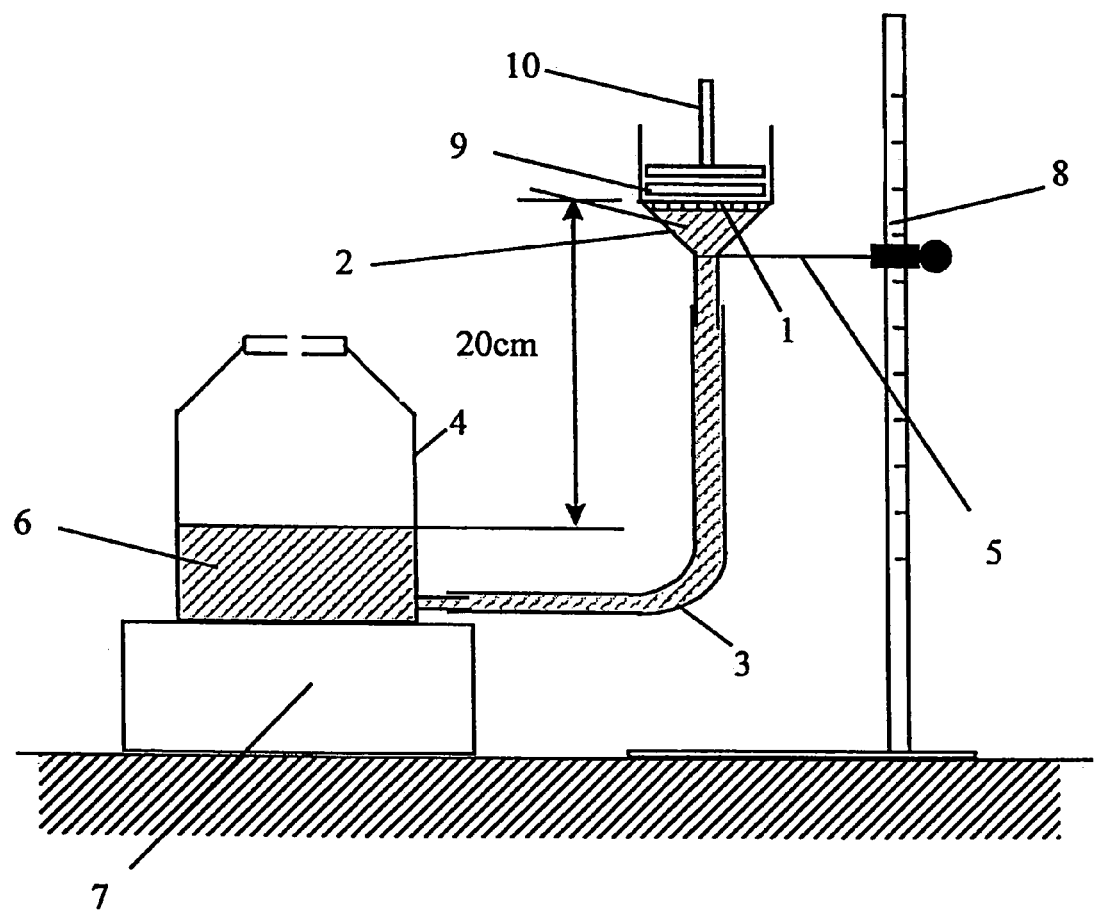
FIG. 1 is a schematic cross section of a measuring device to use in determining the capillary suction force at a height of 20 cm according to the present invention.

This invention primarily concerns a water-absorbent resin composition comprising a water-absorbent resin (R1) obtained by aqueous solution polymerization and a water-absorbent resin (R2) obtained by reversed-phase suspension polymerization or: reversed-phase emulsion polymerization and satisfying any of the following conditions (a)–(c), (a) that capillary suction force capacity of a 0.9 wt. % physiological saline in the gradient of negative pressure of 20 cm be not less than 20 g/g, (b) that a absorption capacity under pressure of a 0.9 wt. % physiological saline under 4.83 kPa at 60 min. be not less than 20 g/g, and (c) that a flow conductivity of a 0.69 wt. % physiological saline be not less than 10 (unit: $10^{-7} \times cm^3 \times s \times g^{-1}$).

Generally, the polymers obtained by reversed-phase suspension and reversed-phase emulsion polymerization assume a spherical form or an aggregate thereof, depending on the mechanism of polymerization thereof and the polymer obtained by aqueous solution polymerization assumes the so-called amorphous form (pulverized form or crushed form). The reversed-phase suspension and reversed-phase emulsion polymerization are inherently carried out in the presence of an emulsifier and a surfactant respectively, the water-absorbent resins consequently remains such surfactant and emulsifier. When the resins are used for an absorbent article, the surfactant and emulsifier effects urine surrounding surface of the resin, thereby decreasing surface tension of the resin. Therefore, the urine flows backward from the resin, the amount of rewet is increased. The mixing of water-absorbent resins produced by different methods of polymerization can adjust the capillary suction force of the gaps among the absorbent resin particles under negative pressure. As a result, the produced mixture excels in absorption properties evaluated in terms of the capillary suction force, the absorption capacity under pressure at 60 minutes, and the flow conductivity of physiological saline. An absorbent article containing this water-absorbent resin composition at a high concentration, therefore, is suggested to manifest well-balanced absorption properties such as high ability to disperse the absorbing fluid, large amount of absorption, and only small amount of rewet. Now, this invention will be described in detail below.

(1) Water-Absorbent Resin

The water-absorbent resin (R1) is obtained by direct polymerization of a monomer in an aqueous solution without using monomer dispersion solvent such as a hydrophobic dispersion solvent. For this production, continuous belt polymerization, continuous batch kneader polymerization, etc. are available. The water-absorbent resin (R2) is obtained by polymerization which causes monomer in an aqueous solution to disperse by suspension or emulsification in a hydrophobic organic solvent. Now, the raw materials and the reaction conditions which are used for the water-absorbent resin of this invention will be described below.

(i) Polymerizable Monomer

As concrete examples of the polymerizable monomer to be used in the water-absorbent resins (R1) and (R2) of this invention, anionically unsaturated monomers such as (meth) acrylic acid, ethacrylic acid, crotonic acid, sorbic acid, maleic acid, itanonic acid, cinnamic acid, vinyl sulfonic acid, styrene sulfonic acid, and vinyl phosphoric acid and slats thereof; nonionic hydrophilic group-containing unsaturated monomers such as 2-hydroxyethyl (meth) acrylate, 2-hydroxypropyl (meth)acrylate, methoxypolyethylene glycol (meth)acrylate, polyethyleneglycol mono(meth)acrylate, N-vinyl pyrrolidone, N-acryloyl piperidine, and N-acryloyl pyrrolidine; and cationically unsaturated monomers such as N,N-dimethylaminoethyl(meth)acrylate, N,N-dimethylaminopropyl(meth)acrylate, alkylene amines, vinyl amines, allyl amines, N-vinyl imidazole, vinyl piridine, vinyl pyridine amine oxide, ethylene imine, and quaternary salts thereof may be cited. When an anionically unsaturated monomer is used as the polymerizable monomer, the salts thereof include alkali metal salts, alkaline earth metal salts, and ammonium salts, for example. While sodium salts, potassium salts, lithium salts, and rubidium salts may be cited as concrete examples of the alkali metal salt, sodium salts or potassium salts prove favorable from the viewpoints of performance of the produced polymer, ease of commercial procurement, and safety. Among the polymerizable monomers mentioned above, acrylic acid and salts thereof prove most favorable.

When the polymerizable monomer to be used is acrylic acid and/or a salt thereof, the component units thereof are preferred to be 0–50 mol % of acrylic acid and 100–50 mol % of an acrylic acid salt (providing that the total thereof will be in the range of 70–100 mol %) and more preferably 10–40 mol % of acrylic acid and 90–60 mol % of an acrylic acid salt. This ratio of the acid and the salt (salt/(acid+salt)) will be referred to as "ratio of neutralization." For the purpose of forming this salt, acrylic acid in the form of a monomer may be neutralized or acrylic acid and an acrylic acid salt may be mixed. Otherwise, a polymerizable monomer may be neutralized as, a polymer during or after polymerization or on both occasions.

(ii) Cross-Linking Monomer

The water-absorbent resin is endowed with a cross-linked structure for the purpose of manifesting the characteristic properties of a water-absorbent resin, but a self-crosslinking type is available. A type obtained by copolymerizing or reacting a cross-linking polymer having not less than two polymerizing unsaturated groups or not less than two reacting groups may be also available. Water-absorbent resin particles resulting from copolymerizing or reacting a cross-linking monomer and possessing a cross-linked structure prove particularly advantageous. As concrete examples of the cross-linking monomer of this sort, N,N'-methylene bis(meth)acrylamide, diethylene glycol di(meth)acrylate, (poly)ethylene glycol di(meth)acrylate, triethylene glycol di(meth)acrylate, propylene glycol di(meth)acrylate, trimethylol propane di(meth) acrylate, trimethylol propane tri (meth) acrylate, pentaerythritol di(meth)acrylate, pentaerythritol tri(meth)acrylate, pentaerythritol tetra(meth) acrylate, (poly)propylene glycol di(meth)acrylate, glycerin tri(meth)acrylate, glycerin acrylate methacrylate, ethylene oxide-modified trimethylol propane tri(meth)acrylate, pentaerythritol tetra(meth)acrylate, dipentaerythritol hexa(meth)acrylate, triallyl cyanurate, triallyl isocyanurate, triallyl phosphate, triallyl amine, poly(meth)allyloxyalkanes, (Poly) ethylene glycol diglycidiny ether, glycerol diglycidyl ether, ethylene glycol, polyethylene glycol, propylene glycol, glycerin, pentaerythritol, ethylene diamine, polyethylene imine, glycidyl(meth)acrylate, triallyl isocyanurate, trimethylol propane di(meth)allyl ether, tetraallyloxy ethane, and glycerol propoxy triacrylate may be cited. These cross-linking polymers may be used in the form of a combination of two or more members. Particularly from the viewpoint of the water absorption property of the water-absorbent resin to be obtained, it is preferable to use a compound possessing not less two polymerizing unsaturated groups as a cross-linking monomer. The amount of this compound to be used is preferably in the range of 0.005–2 mol %, more preferably in the range of 0.01–2 mol %, and most preferably in the range of 0.03–1 mol %, relative to the polymerizable monomer component mentioned above. If the amount of the cross-linking monomer falls short of 0.005 mol % the shortage will possibly prevent the amount of absorption under pressure from reaching a sufficient level because it brings an undue addition to theproportion of the water-soluble component of the produced water-absorbent resin and degrades the strength of a gel which is formed when the resin absorbs water. Conversely, if the amount of the cross-linking monomer exceeds 2 mol %, the excess will prevent the produced water-absorbent resin from acquiring solid state properties fully satisfactory for use because it brings an undue addition to the cross-link density and lowers the absorption capacity of the produced water-absorbent resin.

(iii) Polymerization Initiator

The polymerization initiator which can be advantageously used during the emulsion polymerization of a water-absorbent resin in the present invention comes in two types, water-soluble polymerization initiator and oil-soluble polymerization initiator. As concrete examples of the former type, azo compounds such as 2,2'-azobis(2-amidinopropane) dihydrochloride; persulfates such as ammonium persulfate, potassium persulfate, and sodium persulfate; peroxides such as potassium peracetate, sodium peracetate, potassium percarbonate, and sodium percarbonate; and t-butyl hydroperoxide and hydrogen peroxide may be cited. As concrete examples of the latter type, peroxides such as cumene hydroperoxide, t-butyl hydroperoxide, t-butyl peroxy-2-ethyl hexanoate, di-t-butyl peroxide, diisopropyl benzene hydroxy peroxide, p-menthane hydroperoxide, 1,1,3,3-tetramethyl butyl hydroperoxide, 2,5-dimethyhexane-2,5-dihydroperoxide, benzoyl peroxide, and methylethyl ketone peroxide may be cited.

Besides the radical polymerization initiators mentioned above, activation energy rays such as ultraviolet light and electron ray may be used or a photopolymerization initiator such as 2-hydroxy-2-methyl-1-phenyl-propan-1-on may be used either singly or in combination with an activation energy ray.

When an oxidizing radical polymerization initiator such as is selected from among sodium persulfate and similar persulfates and other peroxides is used, it may be used in combination with a reducing agent in the range of 0–2 mol % based on moles of polymerizable monomer and cross-linking monomer such as a reducing metal salt like sodium sulfite, sodium hydrogen sulfite, or other similar (bi) sulfurous acid (salt), iron sulfate (II), iron chloride (II), or copper chloride (I), amine, L-ascorbic acid (salt), or erisorbic acid (salt) which promotes decomposition of an oxidizing radical polymerization initiator. This combined use is equivalent to using a redox type polymerization initiator. In this invention, the optimum polymerization initiator may be selected, depending on the method of polymerization such as aqueous solution polymerization, reversed-phase suspension polymerization, and reversed-phase emulsion polymerization. The amount of the polymerization initiator to be used is generally in the range of 0.0.01–2 mol % and preferably in the range of 0.01–0.1 mol % based on moles of polymerizable monomer and cross-linking monomer. If the amount of the polymerization initiator to be used falls short of 0.001 mol %, the shortage will be at a disadvantage in unduly increasing the amount of the unaltered monomer and consequently adding to the amount of the residual monomer in the produced water-absorbent resin. Conversely, if the amount of the polymerization initiator exceeds 2 mol %, the excess will be at a disadvantage in rendering the control of polymerization difficult and unduly increasing the amount of the water-soluble component in the produced water-absorbent resin.

The temperature at the time of initiating polymerization is preferably in the range of 15–130° C. and more preferably in the range of 20–120° C., though variable with the kind of polymerization initiator to be used. If the temperature at the time of initiating polymerization or the temperature of polymerization in the course of the reaction deviates from the range mentioned above, the deviation will possibly entail such disadvantages as unduly increasing the amount of the residual monomer in the produced water-absorbent resin, unduly promoting the self-crosslinking reaction, and lowering the absorption capacity of the water-absorbent resin. The duration of the reaction and the pressure of polymerization do not need to be particularly restricted but may be properly set depending on the kind of monomer, the kind of polymerization initiator, and the temperature of reaction.

(iv) Surfactant or Dispersant

As examples of the surfactant or the dispersant to be used in the execution of thee process for reversed-phase suspension and the process for reversed-phase emulsion, anionic surfactants, nonionic surfactants, cationic surfactants, and amphoteric surfactants may be cited.

As concrete examples of the anionic surfactant to be used, fatty acid sodiums such as mixed fatty acid sodium soap and sodium stearate, higher alcohol sodium sulfates, alkyl sodium sulfates, and alkylbenzene sulfonic acid salts may be cited.

As concrete examples of the nonionic surfactant to be used, polyoxyethylene alkyl ethers such as polyoxyethylene higher alcohol ethers, sorbitan fatty acid esters, and glycerin fatty acid esters may be cited.

As concrete examples of the cationic surfactant and the amphoteric surfactant, alkylamines and alkylbetaines may be cited.

As concrete examples of the dispersant, ethyl cellulose an d ethyl hydroxyethyl cellulose may be cited.

Besides, the surfactants and the dispersant which are disclosed in the official gazettes of JP-A-56-93716, JP-A-56-131608, JP-A-57-158209, JP-A-61-115904, JP-A-61-157513, JP-A-61-231003, JP-A-61-231004, JP-A-62-95307, and U.S. Pat. No. 2,574,032 may be sited.

The amount of such surfactant or dispersant to be used may be properly selected, depending on the kind of polymerization. Generally, it is preferably in the range of 1–30 parts by weight and more preferably in the range of 3–5 parts by weight, based on 100 parts by weight of the total monomer component which comprises a polymerizable monomer and a cross-linking monomer. The amount of the dispersant or the surfactant to be used is in the range of 0.001–10% and preferably in the range of 0.001–1%, based on the weight of the organic solvent which will be specifically described here below.

(v) The organic solvent to be used in the execution of the reversed-phase suspension polymerization or the reversed-phase emulsion polymerization does not need to be particularly discriminated but is only required to manifest only sparingly solubility to water and no activity to polymerization. As concrete examples of the organic solvent which answers this description, aliphatic hydrocarbons such as n-pentane, n-hexane, n-heptane, and n-octane, alicyclic hydrocarbons such as cyclohexane and methyl cyclohexane, and aromatic hydrocarbons such as benzene, toluene, and xylene may be cited. Among other organic solvents enumerated above, n-hexane, n-heptane, and cyclohexane prove particularly advantageous from the viewpoint of stability of commercial procurement and quality. The amount of such hydrophobic solvent to be used is in the range of 0.5–10 times, preferably in the range of 0.6–5 times, the amount of the aqueous solution of the polymerizable monomer by weight.

As concrete examples of the organic solvent to be used in the reversed-phase emulsion polymerization, methanol, ethanol, isopropanol, butanol, ethylene glycol monomethyl ether, ethyleneglycol monoethyl ether, propylene glycol monomethyl ether, tetrahydrofuran, dimethylformamide, dimethylsulfoxide, acetone, and methylethyl ketonel may be cited. Among other organic solvents cited above, ethanol and isopropanol prove particularly advantageous.

(vi) Other Components for the Composition

This invention allows the composition to incorporate, besides the polymerizable monomer and the cross-linking monomer mentioned above, deodorant, antibacterial agent, aroma chemical, inorganic powders such as silicon dioxide and titanium oxide, polysaccharides such as starch and cellulose and derivatives thereof, hydrophilic polymers such as polyvinyl alcohol, thermoplastic resins such as polyethylene and polypropylene, foaming agent, pigment, dye, hydrophilic short fibers, plasticizer, and chain transfer agent such as hypophosphorous acid (salt) in an amount of not more than 5% by weight, preferably not more than 1% by weight, based on the weight of the monomer component comprising the polymerizable monomer and the cross-linking monomer.

(vii) Method of Polymerization

The water-absorbent resin (R1) obtained by the aqueous solution polymerization and used in this invention can be produced by any of the following methods ①–④.

① A method which comprises polymerizing a hydrophilic group-containing polymerizable monomer and a cross-linking monomer in an aqueous solution, drying the polymer consequently obtained in the form of a hydrogel, and optionally subjecting the dried polymer to pulverization and surface cross-linking. The polymerization, when necessary for the sake of fitting the purpose, may be carried out with the aqueous solution held in a state having the bubbles of an inert gas dispersed therein in the presence of the polymerization initiator.

② A method which comprises polymerizing a hydrophilic group-containing polymerizable monomer and a cross-linking monomer in an aqueous solution, neutralizing at least part of the carboxyl group in the polymer during or after the polymerization, drying the polymer consequently obtained in the form of a hydrogel, and optionally subjecting the dried polymer to pulverization and surface cross-linking.

③ A method which comprises polymerizing a hydrophilic group containing polymerizable monomer in an aqueous solution, then causing a functional group of the resultant polymer to react with a compound possessing a plurality of functional groups capable of reacting with the functional group of the polymer thereby introducing a cross-linked structure into the polymer, and optionally drying the polymer an subjecting the dried polymer to pulverization and surface cross-linking.

④ A method which comprises polymerizing the product of esterification of a polymerizable monomer and saponifying the resultant polymer before or after cross-linking treatment of the polymer.

Incidentally, the water-absorbent resin (R1) may be produced, besides the methods ①–④ of production mentioned above, by the methods of polymerization disclosed in the official gazettes of JP-A-11-28355, JP-A-11-246625, JP-A-11-333292, JP-A-2000-15093, and JP-A-2000-302876.

The water-absorbent resin (R2) obtained by the reversed-phase suspension or the reversed-phase emulsion polymerization can be produced by the following methods ⑤ and ⑥.

⑤ A method which comprises subjecting a polymerizable monomer including a cross-linking monomer to reversed-phase suspension polymerization in the presence of an organic solvent, a polymerization initiator, and a dispersant.

⑥ A method which comprises subjecting a polymerizable monomer including a cross-linking monomer to reversed-phase emulsion polymerization in the presence of an organic solvent, a polymerization initiator and an emulsifier.

Incidentally, the water-absorbent resin (R2) may be produced by the methods of polymerization disclosed in the official gazettes of JP-A-56-93716, JP-A-56-131608, JP-A-57-158209, JP-A-61-115904, JP-A-61-157513, JP-A-61-231003, JP-A-61-231004, JP-A-62-95307, and U.S. Pat. No. 2,574,032. More preferably, it may be to be produced by the reversed-phase emulsion polymerization.

When the aforementioned monomers are polymerized for the purpose of obtaining the water-absorbent resins (R1) and (R2) to be used in this invention, the polymerization may be implemented in the form of bulk polymerization or precipitation polymerization. From the viewpoint of the aspect of performance, the ease of control of the polymerization, and the absorption properties, however, the polymerization is preferred to proceed on the polymerizable monomer in the form of a solution. In the methods shown in ①–③ and ⑤ and ⑥ mentioned above, the polymerizable monomer is preferred to be polymerized in the form of an aqueous solution. When the polymerizable monomer is used in the form of an aqueous solution, the concentration of the monomer in the aqueous solution does not need to be particularly restricted but may be decided by the temperature of the aqueous solution and the kind of monomer. Nevertheless, it is preferably in the range of 10–70% by weight and more preferably in the range of 20–60% by weight. When the aqueous solution of the monomer is used, it may be used, when necessary, in combination with a solvent other than water. The solvent for this combined use does not need to be particularly discriminated on account of its kind.

In the case of the methods indicated in ①–④ above, a procedure which comprises polymerizing the aqueous solution of the monomer in a twin arm type kneader while crushing the polymer being obtained in the form of a hydrogel or supplying the aqueous solution of the monomer into a prescribed vessel or onto a belt in motion, polymerizing the aqueous solution in the vessel or on the belt, and pulverizing the polymer consequently obtained in the form of a hydrogel as with a meat chopper may be cited.

(viii) Method of Drying

The polymer obtained in the form of a hydrogel during the course or after the completion of the aqueous solution polymerization performed for the purpose of obtaining the water-absorbent resin (R1) contemplated by this invention, when pulverized by a prescribed method into fragments of sizes in the approximate range of 0.1–about 50 mm preferably 0.2–10 mm, more preferably 0.5–5 mm and then dried, can form a water-absorbent resin suitable for the present invention. The temperature for the drying does not need to be particularly restricted, it may be preferably in the range of 100–250° C. and more preferably in the range of 120–200° C. The duration of the drying is properly decided and does not need to be particularly restricted. It is in the approximate range of 10 seconds to five hours and more favorably in the approximate range, of one minute to two hours. The polymer obtained in the form of a hydrogel during the course or after the completion of the reversed-phase suspension or emulsion polymerization performed for the purpose of obtaining the water-absorbent resin (R2) contemplated by this invention is subjected to azeotropic dehydration in a state dispersed in such an organic solvent as a hydrocarbon till the solid content reaches a level exceeding 60% by weight, preferably 70% by weight and thereafter separating the polymer by decantation or distillation from the organic solvent and optionally drying the separated polymer.

A varying method may be adopted without any particular restriction for the purpose of drying. As concrete examples of the method of drying, drying by application of heat, drying by exposure to hot air, drying under a reduced pressure, drying by means of infrared ray, drying by means of microwave, drying with a drum drier, azeotropic dehydration by the use of a hydrophilic organic solvent, and high-humidity desiccation using steam of high temperature may be cited.

(ix) Surface Cross-Linking Treatment

The water-absorbent resin (R1) and/or the water-absorbent resin (R2) contemplated by this invention may be further subjected to a surface cross-linking treatment. The surface cross-linking agent which can be advantageously used in this invention is a cross-linking agent that can react with a carboxyl group. As concrete examples of the cross-linking agent answering this description, polyhydric alcohol compounds such as ethylene glycol, diethylene glycol, propylene glycol, triethylene glycol, polyethylene glycol, 1,3-propane diol, dipropylene glycol, polypropylene glycol, glycerin, polyglycerin, 1,4-butane diol, 1,5-pentane diol, 1,6-hexane diol, and trimethylol propane; epoxy compounds such as ethylene glycol diglycidyl ether, polyethylene glycol diglycidyl ether, glycerol polyglycidyl ether, and propylene glycol diglycidyl ether; polyvalent amind compounds such as ethylene diamine, diethylene triamine, triethylene tetramine, tetraethylene pentamine, polyethylene imine, and polyamide polyamine; haloepoxy compounds such as epichlorohydrin and α-methyl epichlorohydrin; condensates of the polyvalent amine compounds mentioned above with the haloepoxy compounds mentioned above; polyvalent isocyanate compounds such as 2,4-tolylene diisocyanate; polyvalent oxazoline compounds such as 1,2-ethylene bisoxazoline; silane coupling agents such as γ-glycidoxy propyl trimethoxy silane; alkylene carbonate compounds such as 1,3-dioxolan-2-on, 4-methyl-1,3-dioxolan-2-on, and 1,3-dioxan-2-on; oxazolidinone compounds, oxetane compounds, and polyvalent metal salts such as aluminum chloride and aluminum sulfate may be cited, though not exclusively. The polyhydric alcohol compounds, epoxy compounds, polyvalent amine compounds, condensates of polyvalent compounds with haloepoxy compounds, oxetane compounds and alkylene carbonate compounds prove particularly advantageous.

In this invention, these surface cross-linking agents may be used either singly or in the form of a combination of two or more members. The amount of the surface cross-linking agent to be used relative to the water-absorbent resin is preferably in the range of 0.001–10 parts by weight and more preferably in the range of 0.01–5 parts by weight based on 100 parts by weight of the solid component of the water-absorbent resin.

By cross-linking the surface of the water-absorbent resin by the use of the cross-linking agent in the amount falling in the range mentioned above, it is made possible to give a higher cross-link density to the surface of the produced water-absorbent resin than to the interior of the water-absorbent resin and consequently obtain a water-absorbent resin which excels in absorption properties under pressure.

If the amount of the aforementioned cross-linking agent to be used falls short of 0.001 part by weight, the shortage will possibly prevent the effect of improving absorption properties under pressure from being manifested fully satisfactorily because it is incapable of heightening the cross-link density on the surface of the water-absorbent resin above that in the interior of the water-absorbent resin. Conversely, if the amount of the aforementioned cross-linking agent to be used exceeds 10 parts by weight, the excess will possibly lower the amount of absorption greatly under no application of pressure because it is at a disadvantage in not only preventing the added cross-linking agent from being efficiently utilized but also rendering difficult adequate control of the cross-link density on the surface of the water-absorbent resin owing to the excess of the surface cross-linking agent.

The method for adding the surface cross-linking agent does not need to be particularly restricted. Specifically, ① a method which comprises mixing a water-absorbent resin and the cross-linking agent in the absence of a solvent, ② a method which comprises dispersing a water-absorbent resin in a hydrophobic solvent such as cyclohexane or pentane and then mixing the resultant dispersion with a solution of the cross-linking agent in a hydrophilic solvent or hydrophobic solvent, ③ a method which comprises dissolving or dispersing the cross-linking agent in a hydrophilic solvent and then causing the resultant solution or dispersion to be mixed with a water-absorbent resin by means of spraying or dropwise addition, and ④ a method which comprises adding the cross-linking agent to a water-absorbent resin having the water content thereof adjusted in advance to a specific range are concrete, but not exclusive, examples of the method which is available for effecting the addition under discussion. Among other methods enumerated above, the method of ③ proves particularly advantageous for this invention. As the hydrophilic solvent to be used in this case, water or a mixture of water with an organic solvent soluble in water (hydrophilic solvent) proves particularly advantageous. As concrete examples of the organic solvent mentioned above, lower alcohols such as methyl alcohol, ethyl alcohol, n-propyl alcohol, isopropyl alcohol, n-butyl alcohol, iso-butyl alcohol, and t-butyl alcohol; ketones such as acetone; ethers such as dioxane, ethylene oxide (EO) adducts of monohydric alcohols, and tetrahydrofuran; amides such as N,N-dimethylformamide and ε-caprolactam; and sulfoxides such as dimethylsulfoxide may be cited. These organic solvents may be used either singly or in the form of a combination of two or more members. Though the amount of the hydrophilic solvent to be used relative to the water-absorbent resin and the surface cross-linking agent mentioned above is variable with the combination of the water-absorbent resin, cross-linking agent, and hydrophilic solvent, it is preferably not exceeding 200 parts by weight and more preferably falling in the range of 0.001–50 parts by weight, still more preferably in the range of 0.1–50 parts by weight, and particularly preferably in the range of 0.5–30 parts by weight, based on 100 parts by weight of the solid component of the water-absorbent resin.

The mixing device to be used in mixing the water-absorbent resin with a solution containing the cross-linking agent is preferred to be endowed with a large mixing force for the purpose of uniformly and infallibly mixing the two components. As concrete examples of the mixing device which proves advantageous for this invention, cylindrical mixer, double-wall conical mixer, high-speed agitation type mixer, V-shaped mixer, ribbon type mixer, screw type mixer, fluid type rotary disc mixer, air current type mixer, twin arm type kneader, internal mixer, pulverizing kneader, rotary mixer, and screw type extruder may be cited.

For the purpose of increasing the cross-link density on the surface of the water-absorbent resin for use in this invention, the surface cross-linking agent is further added and then heated. Though the temperature of this heating may be properly selected to suit the cross-link density aimed at, it is preferably in the range of 100–250° C. as medium temperature and more preferably in the range of 150–250° C. The duration of this heating is preferably in the range of one minute to two hours. A preferred combination of the heating-temperature and the heating time may be properly selected in the range of 0.1–1.5 hours at 180° C. and in the range of 0.1 to one hour at 200° C.

For the surface cross-linking treatment which is given to the water-absorbent resin, a procedure which comprises subjecting the water-absorbent resin (R1) and the water-absorbent resin (R2) respectively to separate surface cross-linking treatments and a procedure which, depending on the purpose and the necessity thereof, comprises mixing the water-absorbent resin (R1) and the water-absorbent resin (R2) in advance by a method indicated herein below and then subjecting the resultant mixture to a surface cross-linking treatment are available.

(x) Mixing Water-Absorbent Resins (R1) and (R2)

For the preparation of the water-absorbent resin composition of this invention, the water-absorbent resins (R1) and (R2) are mixed at a temperature preferably in the range of 10–150° C. and more preferably in the range of 10–100° C. If this temperature exceeds 150° C., the excess will possibly degrade the absorption properties of the water-absorbent resin and/or the water-absorbent resin composition. Conversely, if the temperature falls smaller under 10° C., the shortage will render the mixing uneconomical because of the problem of cooling. Though the relative humidity during the course of mixing does not need to be particularly restricted, the mixing is preferred to be carried out at a relative humidity in the range of 0–50% RH and preferably in the range of 0–40% RH. The water-absorbent resins (R1) and (R2) are preferred to be mixed by the so-called dry mixture till the solid component reaches a level exceeding 90% by weight, preferably exceeding 95% by weight, and more preferably exceeding 98 weight % without addition of humidity or addition of a solvent such as aqueous liquid during the course of mixing.

By this mixing, a homogeneous mixture of the water-absorbent resins (R1) and (R2) can be realized and a water-absorbent resin composition of a high bulk specific density can be obtained without entailing the phenomenon of segregation. Since the so-called amorphous water absorptive resin (R1) particles and the water-absorbent resin (R2) particles in the form of spheres or an aggregate thereof or in the form of a cluster of grapes are uniformly mixed in a tightly packed state, the resultant mixture befits production of pellets possessing great binding strength where water absorptive particles differing in kind are mutually bound to produce the pellets.

The mixing device to be used in effecting this mixing may mix the water-absorbent resins (R1) and (R2) batchwise or continuously and nevertheless is required to mix the water-absorbent resins (R1) and (R2) uniformly and infallibly. As concrete examples of the mixing device which is used advantageously herein, cylindrical mixer, double wall conical mixer, high speed agitation mixer, V-shaped mixer, ribbon time mixer, screw type mixer, twin arm type kneader, pulverizing kneader, rotary mixer, screw type extruder, batch type redige mixer, fluid bed type mixer and continuous redige mixer may be cited.

(xi) Process of Pelletization

In this invention, before or after the water-absorbent resins (R1) and (R2) are mixed, they may be mixed with such insoluble inorganic particles of $SiO_2$ and a hydrophilic solvent, preferably water, and pelletized.

Though the amount of water to be used in this case varies with the water content of the water-absorbent resins to be used, it is generally in the range of 0.5–20 parts by weight, preferably in the range of 0.5–10 parts by weight, based on 100 parts by weight of the solid contents of the water-absorbent resins. Further, in this invention, a hydrophilic organic solvent may be used besides water. The amount of this hydrophilic organic solvent to be used is in the range of 0–10 parts by weight, preferably in the range of 0–5 parts by weight, and more preferably in the range of 0–3 parts by weight, based on the weight of the mixture of water-absorbent resins mentioned above. The temperature at which the addition of the hydrophilic solvent is effected is preferably in the range of 0–80° C. and more preferably in the range of 40–70° C. for the sake of the ease of mixing. The addition of the hydrophilic solvent to the mixture of water-absorbent resins mentioned above is preferably implemented by spraying or by dropwise addition. The method of spraying is preferred over the method of dropwise addition. The size of the liquid drops of the spray is in the range of 1–300 μm and more preferably 1–200 μm. The addition of the hydrophilic solvent may be carried out in the presence of such an amount of a water-insoluble fine powder or surfactant as will avoid interfering with the effect of this invention.

The mixture of the water-absorbent resins (R1) and (R2) after the addition of the hydrophilic solvent or water thereto is preferably subjected to a heat treatment. As regards the conditions for effecting this heat treatment, the temperature of heating is in the range of 0–260° C., preferably in the range of 100–250° C. and more preferably in the range of 150–250° C. and the duration of heating is preferably in the range of one minute to two hours. Preferred combination of temperature and duration is 0.1–1.5 hours at 180° C. and 0.1–1 hour at 200° C.

The mixing device to be advantageously used for the addition mentioned above is required to produce a large mixing force for the purpose of ensuring uniform mixture. While various mixing devices are usable for the addition of this invention, a high speed agitation type mixer and especially a high speed agitation type continuous mixer prove particularly advantageous. These devices are commercially available under the trademark designations of "Turburizer" produced by HOSOKAWA MICRON Co., and "Redige Mixer" produced by REDIGE Co.

The heat treatment may be carried out by using an ordinary drier or a heating furnace. As concrete examples of the drying device, groove type mixing drier, rotary drier, disk drier, fluidized bed drier, air current type drier, and infrared drier may be cited. The water-absorbent resins which have been heated may be cooled as occasion demands.

(2) Water-Absorbent Resin Composition

The water-absorbent resin composition of this invention is obtained by mixing the water-absorbent resin (R1) and the water-absorbent resin (R2) which have been obtained by the method described above. When necessary, they may be mixed additionally with such additives as pulp, fibrous material, and binder. The ratio of the total amount of the water-absorbent resin (R1) and the water-absorbent resin (R2) to the water-absorbent resin composition is not less than 80% by weight, preferably not less than 90% by weight, and more preferably not less than 95% by weight, and most preferably not less than 98% by weight. Thus, the composition is substantially in a granular form. The water-absorbent resin (R1) and the water-absorbent resin (R2) which jointly form the water-absorbent resin composition contemplated by this invention do not need to be limited to those obtained by the method described above. As the water-absorbent resin (R1), for example, the water-absorbent resins described in the official gazette of JP-A-11-28355, the official gazette of JP-A-11-246625, the official gazette of JP-A-11-333292, U.S. Pat. No. 4,625,001, U.S. Pat. No. 4,873,299, U.S. Pat. No. 4,286,082, U.S. Pat. No. 4,973,632, U.S. Pat. No. 4,985,518, U.S. Pat. No. 5,124,416, U.S. Pat. No. 5,250,640, U.S. Pat. No. 5,264,495, U.S. Pat. No. 5,145,906, U.S. Pat. No. 5,370,808, European Patent No. 0811636, European Patent No. 0955086, and European Patent No.0922717 may be used. As the water-absorbent resin (R2), the water-absorbent resins disclosed in the official gazette of JP-A-11-130968, International Unexamined Patent Publication 2000-513392, U.S. Pat. No. 4,093,776, U.S. Pat. No. 4,367,323, U.S. Pat. No. 4,446,261, U.S. Pat. No. 4,683,274, and U.S. Pat. No. 5,244,735 may be used.

(i) Weight Average Particle Size

The weight average particle size of the water-absorbent resin composition of this invention is preferably in the range of 100–600 μm and more preferably in the range of 100–500 μm. If the weight average particle size exceeds 600 μm, the excess will be at a disadvantage in lowering the speed of absorption during the absorption of urine or body fluid and, when the composition is used as a sanitary material such as disposable diaper, compelling the user: of the sanitary material to experience unpleasant sensation of wear. Conversely, if the weight average particle size falls smaller of 100 μm, the shortage will generally be at a disadvantage in adding to the ratio of fine particles measuring not more than 45 μm.

Owing to the fact that the particle size of the water-absorbent resin composition falls in the range mentioned above coupled with the fact that the water-absorbent resins acquire different shapes on account of difference in method of polymerization, this invention is enabled to obtain a water-absorbent resin composition which secures gaps befitting manifestation of capillarity, enjoys a high ability to effect capillary absorption, secures an outstanding ability to absorb water at a absorption capacity under pressure of not less than 20 g/g, permits compaction of structure, and suffers only from a small amount of rewet. Incidentally, the weight average-particle sizes of the water-absorbent resin (R1) and the water-absorbent resin (R2) may deviate from the range mentioned above so long as the weight average particle size of the water-absorbent resin composition falls in the range mentioned above. They-are preferred in the range of 100–600 μm and more preferably in the range of 100–500 μm.

The particle size of the particle in the water-absorbent resin composition is such that, no matter whether the water-absorbent resin is obtained by the aqueous solution polymerization or by the reversed-phase suspension polymerization or the reversed-phase emulsion polymerization, the water-absorbent resin composition contains particles measuring 850 μm -75 μm preferably at a ratio of not less than 85% by weight, more preferably at a ratio of not less than 90% by weight, and most preferably at a ratio of 95% by weight. Heretofore, a method for decreasing the particle diameter of the particle with a view to increasing the speed of water absorption of the water-absorbent resin and the water-absorbent resin composition has been known to the art. When fine particles measuring less than 75 μm account for a proportion exceeding 15% by weight and particularly fine particles measuring less than 45 μm account for a proportion exceeding 5% by weight, the particles in an absorbent article induce blocking of liquid, obstruct diffusion of the absorbing liquid into the absorbent article, and cause the disposable diaper using the particles to entail leakage. The proportion of the particles measuring less than 45 μm is preferred to be not more than 5% by weight, more preferably not more than 3% by weight, and particularly preferably not more than 1% by weight. If the fine particles measuring less than 45 μm account for a proportion exceeding 5% by weight, the excess will possibly impair greatly the absorption properties of the water-absorbent resin composition because it adds to the surface area of the composition, adds to the contact surface of the composition used as an absorbent article with the ambient air while the article is in use, and renders the article readily soluble in such excretion as urine. Incidentally, the particle in the water-absorbent resin composition includes additives as well as the water-absorbent resin (R1) and the water-absorbent resin (R2).

Incidentally, the particle size contemplated by this invention is determined in accordance with the method which is described in the sub-paragraphs, "Items of determination" and "Method of determination," of working example titled "Weight average particle size" which will be specifically described herein below.

For the purpose of obtaining the water-absorbent resin composition of this invention which possesses such a particle size distribution as this, the procedure of subjecting such amounts of the water-absorbent resin (R1) obtained by aqueous solution polymerization and the water-absorbent resin (R2) obtained by reversed-phase suspension or reversed-phase emulsion polymerization as account for a ratio (R1/R2) in the range of 1/9–9/1, preferably in the range of 9/1–3/7, and more preferably in the range of 9/1–5/5 batchwise or continuously to dry mixing in an atmosphere having a relative humidity of not more than 40% RH ought to suffice.

(ii) Soluble Component

The water-absorbent resin composition of this invention contains the soluble component, namely a component soluble in water and aqueous solution, (otherwise referred to as "water-soluble component") preferably in the range of 0–20% by weight, more preferably in a proportion of not more than 15% by weight. The content of the soluble component (otherwise referred to as "amount of soluble component") varies with the conditions of polymerization such as the amount of a cross-linking agent to be used in the production of a water-absorbent resin to be used in the water-absorbent resin composition mentioned above and the temperature for starting polymerization and the method of polymerization. If the amount of the soluble component exceeds 20% by weight, the excess will be at, a disadvantage in suffering the resin composition, when used as an absorbent article such as disposable diaper, to emit the soluble component by solution into the absorbing liquid during the absorption of water and possibly lowering substantially the absorption capacity, adding to the viscosity of such a liquid as urine, and obstructing the diffusion of the liquid in the absorbent article.

(iii) Absorption Capacity under Pressure (AAP)

The water-absorbent resin composition of this invention has a absorption capacity under pressure of 4.83 kPa of not less than 20 g/g, preferably not less than 23 g/g, and more preferably not less than 25 g/g. The water-absorbent resin composition of this invention is obtained by mixing a water-absorbent resin (R1) and a water-absorbent resin (R2) subjected to a surface cross-linking treatment till the absorption capacity under pressure of 4.83 kPa reaches a level of not less than 20 g/g. For the purpose of realizing the absorption capacity under pressure mentioned above, the water-absorbent resins (R1) and (R2) may be subjected, after they have been mixed, to a surface cross-linking treatment till the absorption capacity under pressure of 4.83 kPa reaches a level of not less than 20 g/g. This invention fixes the pressure under which the absorption capacity is determined at 4.83 kPa because it assumes that the load estimated from the general body weight of a baby (in the neighborhood of 10 kg) falls in the range of 10—several tens of g/cm$^2$. Since the water-absorbent resin composition of this invention excels in bulk specific gravity and compactness and enjoys such a high absorption capacity under pressure as to exceed 20 g/g owing to the use of the mixture of the water-absorbent resins (R1) and (R2), however, it constitutes an optimum water-absorbent resin composition for actual use in a disposable diaper featuring a small thickness and a high performance. It is characterized as well by excelling in the flow conductivity of a 0.69 weight % physiological saline and consequently enjoying a quick rise of the speed of water absorption and suffering from only a very small amount of rewet.

(iv) Capillary Suction Force CSF) and Index of Increase in Capillary Suction Force The term "capillary suction force" as used in the present specification refers to the ability of a water-absorbent resin and a water-absorbent resin composition to absorb a given absorbing liquid against negative pressure. When the water-absorbent resin composition is used as an absorbent article such as disposable diaper, the term expresses the ability of this absorbent article to draw such excretion as urine. The water-absorbent resin composition of this invention is preferred to have a capillary suction force of not less than 20 g/g. The capillary suction force mentioned above is realized by uniformly mixing the so-called irregular-sharp water-absorbent resin (R1) particles and water-absorbent resin (R2) particles in the form of spheres or in the form of a cluster of grapes in a tightly packed state. The CSF is such that, when the water-absorbent resin composition obtained by this invention is used in such an absorbent article as a disposable diaper, it affects the CSF tending to draw the liquid such as urine when it is excreted and, when a baby wearing the disposable diaper continues to stand, it prominently enhances the effect of exalting the force for lifting the liquid up to the upper part of the absorbent article in the disposable diaper, enabling the liquid to be dispersed fully satisfactorily in the absorbent article, and increasing the amount of the absorbing liquid and preventing the liquid from leaking. The CSF of the water-absorbent resin composition of this invention is preferably not less than 20 g/g, more preferably not less than 25 g/g, and particularly preferably not less than 30 g/g.

The term "index of increase in capillary suction force" refers to the ratio of CSF of the water-absorbent resin composition to CSF estimated from CSF of the water-absorbent resin (R1) and the water-absorbent resin (R2) jointly forming the water-absorbent resin composition and the ratio of composition of the water-absorbent resin (R1) and the water-absorbent resin (R2) and it means to express a fluctuation of the CSF of a given water-absorbent resin composition in consequence of the mixture of the water-absorbent resins (R1) and (R2). The index of increase in capillary suction force of the water-absorbent resin composition of this invention exceeds 1.0 and is preferably not less than 1.10 and more preferably not less than 1.15. (v) Flow Conductivity of 0.69 wt. % Physiological Saline (SFC)

The water-absorbent resin composition of this invention is preferred to have the flow conductivity of a 0.69 wt. % physiological saline (SFC) of not less than 10 (unit: $10^{-7} \times cm^3 \times s \times g^{-1}$). The SFC brings an effect to bear on the ability of the water-absorbent resin composition obtained by this invention to pass fluid after the composition is swelled. That is, this ability, when the water-absorbent resin composition of this invention is used in part of an absorbent article such as disposable diaper, enhances the ability of the absorbent article to pass liquid, enables the absorbing liquid to be dispersed fully satisfactorily throughout the absorbent article, increases the amount of absorption of the excretion such as urine while the absorbent article is in use, and prominently improves the effect of preventing the liquid from leakage. The SFC is preferably not less than 10 (unit: $10^{-7} \times cm^3 \times s \times g^{-1}$) and more preferably not less than 15 (unit: $10^{-7} \times cm^3 \times s \times g^{-1}$).

The terms "soluble component," "absorption capacity under pressure," "capillary suction force (CSF)", "index of increase of capillary suction force," "and "flow conductivity of 0.69wt. % physiological saline (SFC)" as used in the subject patent application respectively represent "soluble component," "absorption capacity under pressure(AAP)," "capillary suction force (CSF)," "index of increase in capillary suction force," and "flow conductivity of a 0.69 wt. % physiological saline (SFC)" which are defined in the working example cited herein below.

The water-absorbent resin composition of this invention satisfies preferably not less than two of the magnitudes of "absorption capacity under pressure (AAP)," "capillary suction force (CSF)," "index of increase in capillary suction force," and "flow conductivity of a 0.69 wt. % physiological saline (SFC)" indicated above, more preferably the combination of CSF and AAP and the combination of CSF and SFC, and still more preferably not less than three of the magnitudes.

(3) Method for Production of Water-Absorbent Resin Composition Excelling in CSF or SFC The water-absorbent resin composition which, as described above, is the mixture of a water-absorbent resin (R1) obtained by aqueous solution polymerization and a water-absorbent resin (R2) obtained by reversed-phase suspension or reversed-phase emulsion polymerization and possesses the mixture's absorption capacity under pressure of not less than 20 g/g. It excels in CSF and SFC. This statement signifies that when a resin composition of this sort is aimed at a absorption capacity under pressure of not less than 20 g/g, it gives rise to a water-absorbent resin composition having a capillary suction force (CSF) of not less than 20 g/g or an flow conductivity of a 0.69 wt. % physiological saline (SFC) of not less than 10 (unit: $10^{-7} \times cm^3 \times s \times g^{-1}$). In the method for production mentioned above, the water-absorbent resin (R1) and the water-absorbent resin (R2) are preferred to be mixed by dry mixing.

(4) Use (i) Water-Absorbent Articles

The water-absorbent resin composition of this invention, when composed together with such a fibrous material as pulp, is transformed into a molded water absorbent article. The water absorbent article is molded in the shape of sheets, layers, tape strips, and cylinders. As concrete examples of the water absorbent article so obtained by molding, sanitary materials (humor absorbent articles) such as disposable diapers, sanitary napkins, pads for use by patients of incontinence with a view to precluding the possible leakage of excretion, materials for protecting wounds against external harms, and materials for curing wounds; absorbent articles for urine of pets; materials for civil engineering and construction such as building materials, materials for water retention in soil, materials for stopping water flow, packing materials, and gel water pouches; articles for food stuffs such as drip absorbers, freshness retaining materials, and heat insulating materials; various industrial articles such as oil-water separating materials, antifreezing materials, and coagulating materials; and agricultural/horticultural articles such as materials for retaining water in plants and soil may be cited. These uses do not need to be restricted exclusively.

(ii) Disposable Diaper

The disposable diaper using the water-absorbent resin composition of this invention is formed, for example, by laminating a back sheet (backing member) made of a material impervious to liquid, a core layer (absorbing member) comprising a water-absorbent resin of this invention and a fibrous material, and a top sheet (surface member) formed of a material pervious to liquid sequentially in the order mentioned, fixing them mutually, and imparting a gather (elastic member) or attaching a tape fastener to the resulting laminate as well. The term "disposable diaper" embraces an infant's pants having appended thereto a disposable diaper to be used in accustoming an infant to the excretion of urine and the defecation. The water-absorbent resin of this invention has a high ratio of water absorption to pressure resistance and, therefore, can be used as a high concentration core [water-absorbent resin/(fibrous base material+water-absorbent resin); wt/wt) in a disposable diaper. This concentration is in the range of 30–100%core, more preferably in the range of 40–95% core, and particularly in the range of 50–90% core. Owing to this concentration, the disposable diaper can be finished in a small wall thickness.

(iii) Others

The water-absorbent resin composition of this invention can incorporate therein various additives such as deodorant, antibacterial agent, chelating agent, perfume, various inorganic powder, foaming agent, pigment, dye, hydrophilic short fibers, fertilizer, oxidizing agent, reducing agent, water, and varying salt in the range of 0–30% by weight, preferably 0–10% by weight with the object of imparting various functions to the produced water absorbent article.

EXAMPLES

Now, this invention will be described more specifically below with reference to working examples and comparative examples. This invention does not need to be restricted to these working examples but may allow alterations thereof without departure from the scope of the invention. The capillary suction force, the bulk specific gravity, the flow conductivity of 0.69 wt % physiological saline, the absorption capacity under no pressure, the absorption capacity under pressure, the weight average particle size, and the soluble component indicated in the examples are determined by the following methods. The "parts" means "parts by weight" unless otherwise specified.

Method of Determination (1) Capillary Suction Force (Capillary Suction Force under the Gradient of Negative Pressure of 20 cm of 0.9 Weight % Physiological Saline (CSF))

The capillary suction force contemplated by this invention is determined by measuring the ability of a given water-absorbent resin or water-absorbent resin composition to absorb liquid under the gradient of negative pressure of 20 cm within a prescribed duration of time under a load of 0.06 psi (0.41 KPa). The device and the method for measuring the capillary suction force will be described below with reference to FIG. 1.

1) A conduit 3 is rigged to the lower part of a glass filter 2 measuring 60 mm in diameter and furnished with a liquid absorbing surface made of a porous glass sheet 1 (Glass Filter Particle No. #3: Buchner type filter TOP 17G-4 (code no. 1175-03) made by Sogo Rikagaku Glass Seisakusho) and this conduit 3 is connected to a mouth provided in the lower part of a liquid reservoir 4 measuring 10 cm in diameter. The porous glass sheet 1 of the glass fiber 2 mentioned above has pores of an average diameter in the range of 20–30 μm. By the capillary force of the porous glass sheet 1, the porous glass sheet 1 can retain water therein in spite of the negative pressure of the water column even in the state having a difference of level of 60 cm and can retain the state having no introduction of air. A supporting ring 5 adapted to fluctuate height is attached to the glass filter 2, the system is filled with physiological saline (0.9 wt. % NaCl solution) 6, and the solution reservoir 4 is mounted on a balance 7. The interior of the conduit 3 and the lower part of the porous glass sheet 1 of the glass filter 2 are visually inspected to conform absence of air and then the difference of height between the level of liquid in the upper part of the physiological saline (0.9 wt. % NaCl solution) 6 in the liquid reservoir 4 and the level in the upper part of the porous glass sheet 1 is adjusted to 20 cm and then the glass filter 2 is fixed to a stand 8.

2) Under the conditions of 25±1° C. in temperature and 60±5% RH in humidity, 0.44 g of a given sample (water-absorbent resin or water-absorbent resin composition) is quickly dispersed on the porous glass sheet 1 and a load 10 (0.419 kPa) measuring 59 mm in diameter is placed on the spread layer of the sample and allowed to stand on the sample for 30 minutes. After the elapse of 30 minutes, the amount ($W_{30}$) of the physiological saline (0.9 wt. % NaCl solution) absorbed in the sample 9 is measured. The capillary suction force can be found by the following formula.

Ratio of capillary suction force (g/g)=Amount absorbed ($W_{30}$)g/0.44 (g)

From the capillary suction force found by the preceding formula, the index of increase of capillary suction force defined by the following formula is found.

Index of increase in cappillary suction force=(CSF of water-absorbent resin composition)/(CSF of water-absorbent resin (R1) forming water-absorbent resin composition)×(wt. % of water-absorbent resin (R1) in water-absorbent resin composition÷100)+(CSF of water-absorbent resin (R2) forming water-absorbent resin composition)×(wt. % of water-absorbent resin (R2) in water-absorbent resin composition÷100)

(2) Bulk Specific Gravity

The bulk specific gravity of a given water-absorbent resin or water-absorbent resin composition is determined in accordance with the method disclosed in the official gazette of JP-A-2000-302876 by following JIS (Japanese Industrial Standard K3362 (1998 ed.) using a bulk density gravity tester (made by Kuramochi Kagaku Kikai Seisakusho).

(3) Flow Conductivity of 0.69 wt. % Physiological Saline (SFC)

This magnitude is determined by following the test for the flow conductivity of 0.69 wt. % physiological saline (SFC) disclosed in the official gazette of International Unexamined Patent Publication No. 9-509591.

Figure 2:
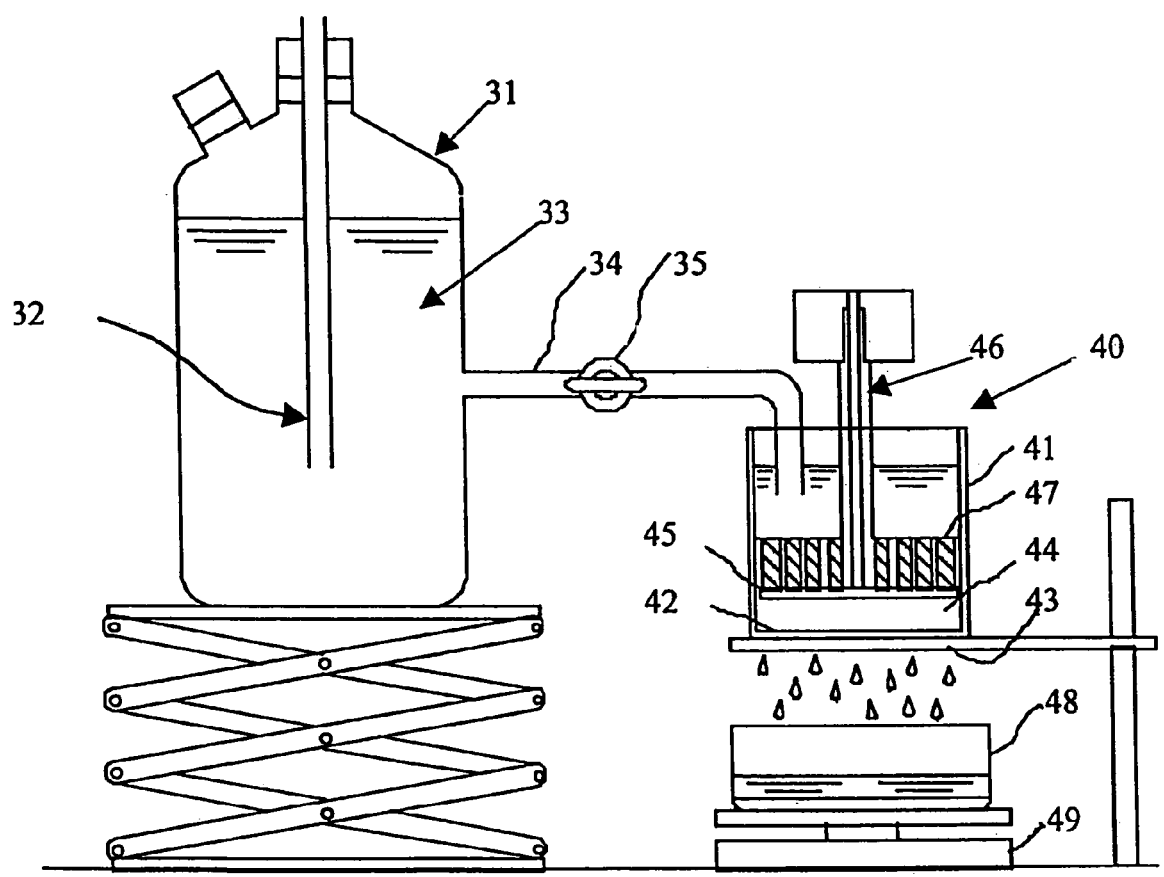
FIG. 2 is a schematic cross section of a measuring device to use in determining the amount of permeability pressure.

In a device illustrated in FIG. 2, a given water-absorbent resin or water-absorbent resin composition (0.900 g) placed uniformly in a container 40 is left standing in artificial urine (1) under application of a pressure of 0.3 psi (2.07 kPa) for 60 minutes to be impregnated therewith. The height of a gel layer of swelled gel 44 is recorded. Then, an aqueous 0.69 wt. % sodium chloride solution 33 from a tank 31 is passed through the layer of swelled gel under a prescribed hydrostatic pressure. This SFC test is carried out at normal room temperature (20–25° C.). By the use of a computer and a balance, the amount of liquid passing the gel layer is recorded as the function of time for 10 minutes at intervals of 20 seconds. The flow velocity $F_s$ (t) mainly through the gaps between the adjacent particles of the welled gel 44 is decided in the units of g/s by dividing the increased weight (g) by the increased duration (s). By using $t_s$ as the symbol for designating the time at which a prescribed hydrostatic pressure and a stable flow velocity are obtained, using only the data obtained during the period of 10 minutes following $t_s$ for the calculation of flow velocity, and using the flow velocity obtained during the 10 minutes following $t_s$, the magnitude of $F_s$ (t=0), namely the first flow velocity through the gel layer, is computed. $F_s$ (t=0) is computed by extrapolating the results of the least squares method applied to $F_s$ (t) vs. time into t=0.

Flow conductivity of 0.69 wt. % physiological saline $(10^{-7} \times cm^3 \times s \times g^{-1})=(F_s(t=0) \times L_o)/(\rho \times A \times \Delta P)=(F_s(t=0) \times L_o)/139506$ wherein $F_s$ (t=0): Flow velocity expressed in g/s $L_o$: Height of gel layer expressed in cm ρ: Density of NaCl solution (1.003 g/cm$^3$)

A: Surface area of the upper side of the gel layer in a cell 41 (28.27 cm$^2$)

ΔP: Hydrostatic pressure exerted on gel layer (4920 dynes/cm$^2$)

In the device illustrated in FIG. 2, a glass tube 32 is inserted into a tank 31 and the glass tube 32 has the lower end thereof so disposed as to retain the aqueous 0.69 wt. % sodium chloride solution 33 at a height of 5 cm from the bottom part of a swelled gel 44 in the cell 41. The aqueous 0.69 wt. % sodium chloride solution 33 in the tank 31 is supplied via an L-shaped tube 34 fitted with a cock to the cell 41. A container 48 for collecting the passing liquid is disposed beneath the cell 41 and the collecting container 48 is mounted on a pan scales 49. The cell 41 measure 6 cm in inside diameter and has disposed on the bottom surface in the lower part thereof a No. 400 stainless steel gauze (aperture 38 μm) 42. A piston 46 is provided in the lower part thereof with holes 47 enough for passing liquid and in the bottom part thereof with a glass filter 45 of generous permeability so that water-absorbent resin such as a water absorbing agent or a swelled gel thereof should not enter the holes 47. The cell 41 is mounted on a stand for supporting it. The surface of the stand destined to contact the cell is mounted on a metallic gauze 43 made of stainless steel lest it should interfere with the passage of liquid.

Incidentally, the artificial urine (1) mentioned above is formed by joining 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and .994.25 g of purified water together.

(4) Absorption Capacity under no Pressure (Absorption Capacity by Absorption of 0.90 wt. % Physiological Saline Continued for 30 Minutes under no Pressure (GV))

Under the conditions of room temperature (20–25° C.) and humidity of 50 RH %, 0.20 g of a water-absorbent resin or water-absorbent resin composition is uniformly placed in a pouch (60 mm×60 mm) made of nonwoven fabric, sealed, and then left immersed in 0.9 wt. % hysiological saline at room temperature. After the elapse of 30 minutes thence, the pouch is pulled out, strained by the use of a centrifugal separator (made by Kokusan K.K. and sold under the trademark designation of "Centrifuge, Model H-122") at 250 G for three minutes, and weighed to fine the weight $W_1$ (g). The same procedure is repeated without using either water-absorbent resin or water-absorbent resin composition to determine the weight $W_0$ (g) at that time. The absorption capacity under no pressure (g/g) is computed in accordance with the following formula using these magnitudes, $W_1$ and $W_0$.

Absobenion capacity under no pressure (g/g)=($W_1$(g)–$W_0$(g) /weight (g) of water-absorbent resin or water-absorbent resin composition (5) Absorption Capacity under Pressure (Absorption Capacity of 0.90 wt. % Physiological Saline Continued for 60 Minutes under 4.83 kPa (AAP))

A 400-mesh metallic gauze (aperture 38 μm) made of stainless steel is fused to the bottom of a supporting cylinder made of plastic material and measuring 60 mm in inside diameter, 0.90 g of a water-absorbent resin or water-absorbent resin composition is uniformly sprayed on the metallic gauze under the conditions of room temperature (20–25° C.) and 50 RH % in humidity, and a piston adjusted to exert uniformly a load of 4.83 kPa (0.7 psi) on the water-absorbent resin or water-absorbent resin composition, furnished with an outside diameter slightly smaller than 60 mm, precluded from forming a gap with the inner wall of the supporting cylinder, and enabled to produce a vertical motion without obstruction is mounted thereon together with a load sequentially in the order mentioned to complete a measuring device. The weight $W_a$ (g) of the entire system of this measuring device is measured.

A glass filter measuring 90 mm in diameter (containing fine pores 100–120 μm in diameter: made by Sogo Rikagaku Glass Seisakusho K.K.) is placed inside a petri dish measuring 150 mm in diameter and 0.90 wt. % physiological saline (20–25° C.) is added thereto till it rises to a level flush with the upper surface of the glass fiber.

One filter paper measuring 90 mm in diameter (having a thickness of 0.26 mm and retaining particles 5 μm in diameter; made by ADVANTEC Toyo K.K. and sold under trademark designation of "JIS P3801, No. 2") is mounted thereon and allowed to have the surface completely wetted and is drained to expel excess liquid.

The whole system of the measuring device mentioned above is mounted on the wetted filter paper and enabled to absorb the liquid under the load. After the elapse of one hour thence, the whole system of the measuring device is lifted from the filter paper and weight to find the weight $W_b$ (*g). The absorption capacity under pressure (g/g) is computed in accordance with the following formula, using $W_a$ and $W_b$.

Absorption capacity under pressure (g/g) =($W_b$ (g)–
($W_a$ (g) /weight of water-absorbent resin or
water-absorbent resin composition ((0.9) g).

(6) Weight Average Particle Size

A given water-absorbent resin powder or water-absorbent resin composition is classified with JIS standard sieves having varying apertures of 850 μm, 600 μm, 500 μm, 425 μm, 300 μm, 212 μm, 150 μm, 106 μm, and 75 μm. The residual percentage ratios R consequently found are plotted on a logarithmic probability chart. The weight average particle size (D50) is read out of the chart.

As regards the screening and the method of classification adopted in determining the SFC for each of the particle sizes which will be more specifically described herein below, JIS standard sieves (sold under the trademark designation of "THE IIDA TESTING SIEVE,: 8 cm in diameter) having apertures of 850 μm, 600 μm, 500 μm, 300 μm, and 150 μm are each charged with 10.0 g of a water-absorbent resin powder or a water-absorbent resin composition under the conditions of room temperature (20–25° C.) and 50 RH % in humidity and shaken with a shaking classifier (sold under the trademark designation of "IIDA SIEVE SHAKER, Type ES-65, Ser No. 0501") for 10 minutes to classify the sample. The term "weight average particle size (D50)" means the particle diameter of a standard sieve of a specific aperture corresponding to 50 wt. % of all the particles in the standard sieve as described in U.S. Pat. No. 5,051,259, for example. When a standard sieve having an aperture of 300 μm, for example, classifies 50 wt. % of all the particles, the weight average particle size (D50) is 300 μm.

(7) Soluble Component

In a lidded plastic container having an inner volume of 250 ml, 184.3 g of an aqueous 0.9 wt. % physiological NaCl solution (physiological saline) is placed and 1.00 g of a water-absorbent resin is added to the aqueous solution and they are stirred together for 16 hours to extract the soluble component from the resin. The extracted solution is filtered through one filter paper (having a thickness of 0.26 mm and retaining particles 5 μm in diameter; made by ADVANTEC Toyo K.K. and sold under trademark designation of "JIS P3801, No. 2"). A portion, 50.0 g, is weighed out of the filtrate and used as a sample solution for measurement.

First, the physiological saline alone is titrated with an aqueous 0. 1N NaOH solution till pH 10. Then, it is titrated with an aqueous 0.1N HCl solution till pH 2.7 to obtain a blank titer ([bNaOH] ml, [bHCl] ml)

By performing the same procedure of titration on a sample solution for measurement, a titer ([NaOH] ml, [HCl] ml) is found.

In the case of a water-absorbent resin or water-absorbent resin composition formed of known amounts of acrylic acid and a sodium salt thereof, for example, the soluble component in the water-absorbent resin or water-absorbent resin composition can be calculated in accordance with the following formula using the average molecular weight of the monomer and the titer obtained by the procedure mentioned above. When the amounts mentioned above are unknown, the average molecular weight of the monomer can be calculated by using the ratio of neutralization found by titration. Incidentally, in a case of water-absorbent resin excluding acidic group, it is calculated by using the weight of filtrate.

Soluble component (wt. %)=0.1×(average molecular weight)×184.3×100×([HCl]–[bHCl])/1000/1.0/50.0

Ratio of neutralization (mol %)=(1–([NaOH]–[bNaOH])/([HCl]–[bHCl])×100

(8) Amount of Rewet of Water-Absorbent Resin or Water-Absorbent Resin Composition In a glass petri dish measuring 9 cm in diameter, a 1.0 g sample weighed out of a water-absorbent resin or water-absorbent resin composition is uniformly scattered. Then, 30 g of artificial urine (2) at room temperature is poured into the petri dish holding the sample. The artificial urine (2) is an aqueous solution containing 1.9 wt. % of urea, 0.8 wt. % of sodium chloride, 0.1 wt. % of calcium chloride, and 0.1 wt. % of magnesium sulfate.

After the elapse of 30 minutes thence, a circular piece 9 cm in diameter cut from nonwoven fabric is placed on the upper surface of a swelled gel of water-absorbent resin or water-absorbent resin composition and 10 preweighed filter papers 9 mm in diameter (having a thickness of 0.26 mm and retaining particles 5 μm in diameter; made by ADVANTEC Toyo K.K. and sold under trademark designation of "JIS P3801, No. 2") are mounted thereon, and a weight of a load of 500 g (15 g/cm²) is placed on the filter papers and left standing for one minute. After the elapse of one minute thence, the 10 filter papers are weighed to find their weight to determine the amount of rewet of the water-absorbent resin or water-absorbent resin composition (amount retrograded (g)).

Referential Example 1

Method for Production of Water-Absorbent Resin A

A reaction solution was obtained by dissolving 8.1 parts of polyethylene glycol diacrylate (n=8) in 5500 parts of an aqueous 38 wt. % sodium acrylate solution (ratio of neutralization 71 mol %). Then, this reaction solution was deaerated in an atmosphere of nitrogen gas for 30 minutes. Then, the reaction solution mentioned above was supplied to a twin arm type kneader made of stainless steel, fitted with a closable lid, and provided with two sigma type vanes. The system was displaced with nitrogen gas with the solution kept at 30° C. Subsequently, the reaction solution was kept stirred and 2.4 parts of ammonium persulfate and 0.12 part of L-ascorbic acid were added to the stirred reaction solution. After the elapse of about one minute thence the reaction solution began polymerizing. Then, the polymerization was carried out at 20–95° C. of peak temperature. After the elapse of 60 minutes following the start of polymerization, a polymer of the form of hydrogel was taken out.

The polymer thus produced in the form of hydrogel was in a state finely divided into fragments about 0.5–5 mm in diameter. The finely divided polymer of the form of hydrogel was spread on a metallic gauze of 50 mesh (aperture 300 μm) and dried with hot air at 150° C. for 90 minutes. Then, the dried polymer was pulverized by the use of a roll granulator type pulverizer whose pulverizing rolls were disposed on three stages so as to be separated with prescribed intervals (roll gap about 1.63 mm, about 0.43 mm and about 0.15 mm) and further passed through a sieve of an aperture of 850 μm to obtain a water-absorbent resin A' crashed in an irregular sharpe.

One hundred parts of the produced water-absorbent resin A' and a solution of a cross-linking agent composition formed of 0.3 part of 1,4-butane diol, 0.5 part of propylene glycol, and 3 parts of water were mixed together. The mixture thus obtained was heated at 210° C. for 30 minutes and then passed through a sieve having an aperture of 850 μm to obtain a water-absorbent resin A. The particle size, GV, AAP, SFC, and soluble component of each of:the water-absorbent resins obtained in the working examples, comparative examples, and reference examples to be cited herein below are shown in Tables 1–6 and FIGS. 3–5, the bulk specific gravity thereof in Tables 7–9, the CSF thereof in Tables 10–12, the index of increase of capillary suction force in Tables 11 and 12, and the amount of rewet in Tables 13–15.

Referential Example 2

Method for Production of Water-Absorbent Resin B

A reaction solution was obtained by dissolving 8.3 parts of polyethylene glycol diacrylate (n=8) in 5500 parts of an aqueous 33 wt. % sodium acrylate (ratio of neutralization 75 mol %) solution. Then, this reaction solution was deaerated in an atmosphere of nitrogen gas for 30 minutes. Subsequently, the reaction solution mentioned above was supplied to a twin arm type kneader made of stainless steel, fitted with a closable lid, and provided with two sigma type vanes. The reaction solution was kept at 30° C. and the system was displaced with nitrogen gas. Then, the reaction solution was kept stirred and 2.4 parts of ammonium persulfate and 0.12 part of L-ascorbic acid were added to the stirred reaction solution. After the elapse of about one minute thence, the reaction solution began polymerizing. Then, the polymerization was carried out at 30–90° C. After the elapse of 60 minutes following the start of polymerization, a polymer in the form of hydrogel was taken out.

The polymer thus produced in the form of hydrogel was in a state finely divided into fragments about 5 mm in diameter. The finely divided polymer of the form of hydrogel was spread on a 50-mesh metallic gauze (aperture 300 μm) and dried with hot air at 150° C. for 90 minutes. Then, the dried polymer was pulverized by the use of a shaking mill and further classified with a metallic gauze having an aperture of 850 μm to obtain a water-absorbent resin B' in a state crushed into an amorphous form.

One hundred (100) parts of the produced water-absorbent resin B' and a solution of a cross-linking agent composition formed of 0.05 part of ethylene glycol diglycidyl ether, 0.75 part of glycerin, 3 parts of water, 0.3 part of lactic acid, and 1 part of isoproplyl alcohol were mixed together. By heat-treating the mixture at 195° C. for 40 minutes and then passing it through a sieve having an aperture of 850 μm, a water-absorbent resin B was obtained.

Referential Example 3

Method for Production of Water-Absorbent Resin C

An aqueous monomer solution having a monomer concentration of 35 wt. % and a ratio of neutralization of 75 mol % was obtained by using 21.6 parts of acrylic acid, 228.6 parts of an aqueous 37 wt. % sodium acrylate solution, 0.0185 part of N,N'-methylene bisacrylamide (0.01 mol % based on the monomer), 0.106 part of hydroxyethyl cellulose, and 53 parts of deionized water. The dissolved oxygen in the aqueous monomer solution was expelled by having 0.09 part of potassium persulfate dissolved therein and blowing nitrogen gas therein.

In a four-neck separable flask fitted with a stirrer, a reflux condenser, a thermometer, a nitrogen gas inlet tube, and a dropping funnel, 800 parts of cyclohexane was placed, 4 parts of sucrose fatty acid ester (HLB=6) as a dispersant was dissolved therein, and nitrogen gas was blown in to expel the dissolved oxygen. Then, the aqueous monomer solution was added while in a stirred state into the separable flask mentioned above and dispersed therein. Thereafter, the bath temperature was elevated to 65° C. to initiate a reaction of polymerization. Thereafter, the polymerization was completed by retaining this temperature for two hours. After the polymerization was completed, the solution of the resultant polymer was deprived of the greater part of the water content by azeotropic dehydration, then filtered, and further dried under a reduced pressure at 100° C. to obtain a water-absorbent resin C' having a water content of 8%. A water-absorbent resin C was obtained by mixing 100 parts of the water absorptive resin C', 0.1 part of ethylene glycol diglycidyl ether, 3 parts of water, and 1 part of isopropanol, heating the resultant mixture at 120° C. for 30 minutes, and treating the particles consequently formed with methanol.

Referential Example 4

Method for Production of Water-Absorbent Resin D

An aqueous monomer solution having a monomer concentration of 35 wt. % and a ratio of neutralization of 75 mol % was obtained by using 21.6 parts of acrylic acid, 228.6 parts of an aqueous 37 wt. % sodium acrylate solution, 0.0148 part of N,N'-methylenebisacryl amide (0.008 mol % based on the monomer), 0.106 part of hydroxyethyl cellulose, and 53 parts of deionized water. The dissolved oxygen in the aqueous monomer solution was expelled by having 0.09 part of potassium persulfate dissolved therein and blowing nitrogen gas therein.

In a four-neck separable flask fitted with a stirrer, a reflux condenser, a thermometer, a nitrogen gas inlet tube, and a dropping funnel, 800 parts of cyclohexane was placed, 4 parts of sucrose fatty acid ester (HLB=6) as a dispersant was added thereto, and nitrogen gas was blown in to expel the dissolved oxygen. Then, the aqueous monomer solution was added while in a stirred state to the separable flask mentioned above and disperse therein. Thereafter, the bath temperature was elevated to 65° C. so as to initiate a reaction of polymerization. Then, this polymerization was completed by keeping this temperature for two hours. After the polymerization was completed, the solution of the produced polymer was deprived of the greater part of the water content by azeotropic dehydration, filtered, and further dried under a reduced pressure at 100° C. to obtain a water-absorbent resin D' having a water content of 8%. A water-absorbent resin D was obtained by mixing 100 parts of the water-absorbent resin D', 0.1 part of ethylene glycol diglycidyl ether, 3 parts of water, and 1 part of isopropanol, heating the resultant mixture at 120° C. for 30 minutes, and then treating the particles consequently formed with methanol.

Referential Example 5

Method for Production of Water-Absorbent Resin E

An aqueous monomer solution having a monomer concentration of 35 wt. % and a ratio of neutralization of 75 mol % was obtained by using 21.6 parts of acrylic acid, 228.6 parts of an aqueous 37 wt. % sodium acrylate solution, 0.0056 part of N,N'-methylenebisacryl amide (0.003mol % based on the monomer), 0.106 part of hydroxyethyl cellulose, and 53 parts of deionized water. The dissolved oxygen in this aqueous monomer solution was expelled by having 0.09 part of potassium persulfate dissolved therein and blowing nitrogen gas.

In a four-neck separable flask fitted with a stirrer, a reflux condenser, a thermometer, a nitrogen gas inlet pipe, and a dropping funnel, 800 parts of cyclohexane was placed, 4 parts of sucrose fatty acid ester (HLB=6) as a dispersant was added together and dissolved therein, and nitrogen gas was blown therein to expel the dissolved oxygen. Then, the aqueous monomer solution was added while in a stirred state to the separable flask mentioned above and dispersed therein. Then, the bath temperature was elevated to 65° C. to initiate a reaction of polymerization. This polymerization was completed by keeping this temperature for two hours. After the polymerization was completed, the solution of the polymer was deprived of the greater part of the water content by azeotropic dehydration, filtered, and further dried under a reduced pressure at 100° C. till a constant volume was reached. To obtain a water-absorbent resin E' having a water content of 8%. A water-absorbent resin E was obtained by mixing 100 parts of the water-absorbent resin E' thus obtained, 0.1 part of ethylene glycol diglycidyl ether, 3 parts of water and 1 part of isopropalnol together, heating the resultant mixture at 120° C. for 30 minutes, and treating the particles consequently formed with methanol.

Referential Example 6

Method for Production of Water-Absorbent Resin f

An aqueous monomer solution having a monomer concentration of 35 wt. % and a ratio of neutralization of 75 mol % was obtained by using 21.6 parts of acrylic acid, 228.6 parts of an aqueous 37 wt. %sodium acrylate solution, 0.0185 part of N,N'-methylene bisacrylamide (0.01 mol % based on the monomer) 0.106 part of hydroxyethyl cellulose, and 53 parts of deioized water. The dissolved oxygen in the aqueous monomer solution was expelled by having 0.09 part of potassium persulfatae dissolved therein and blowing nitrogen gas therein till the concentration of dissolved oxygen reduced less than 1 ppm.

In a four-neck separable flask fitted with a stirrer, a reflux condenser, a thermometer, a nitrogen gas inlet pipe, and a dropping funnel, 800 parts of cyclohexane was placed, 4 parts of sucrose fatty acid ester (HLB=6) as a dispersant was added thereto and dissolved therein, and nitrogen gas was blown therein to expel the dissolved oxygen. Then, the aqueous monomer solution was added while in a stirred state into the separable flask mentioned above and dispersed therein. Thereafter, the bath temperature was elevated to 65° C. to initiate a reaction of polymerization. This polymerization was completed by keeping this temperature for two hours. After the polymerization was completed, the solution of the polymer was deprived of the greater part of the water content by azeotropic dehydration, filtered, and further dried under a reduced pressure at 120° C. till a constant volume was reached to obtain a water-absorbent resin F.

Referential Example 7

Method for Production of Water-Absorbent Resin G

A water-absorbent resin G was obtained by passing the water-absorbent resin B obtained in Referential Example 2 through a sieve having an aperture of 106 μm.

Referential Example 8

Method for Production of Water-Absorbent Resin H

A water-absorbent resin H was obtained by mixing 100 parts of the water-absorbent resin B' obtained in Referential Example 2 and a solution of a surface cross-linking agent composition formed of 0.1 part of ethylene glycol diacrylate, 0.3 part of proplylene glycol; and 3 parts of water together, heating the resultant mixture at 195° C. for 30 minutes, passing the heated mixture through sieves having apertures of 500 μm and 106 μm, and classifying the separated particles with sieves of 500 μm and 106 μm.

Example 1

A water-absorbent resin composition (1) was obtained by introducing 30 parts of the water-absorbent resin A obtained in Referential Example 1 and 70 parts of the water absorptive Resin C obtained in Referential Example 3 at a relative humidity of 40% RH into a Redige mixer (made by Redige Corp and sold under the product code of "Type M5R") and stirring them at 330 rpm for 15 seconds.

Example 2

Water-absorbent resin compositions (2)–(11) were obtained by mixing the water-absorbent resins A–E obtained in Referential Examples 1–7 at composition ratios indicated in Table 8 by following the procedure of Example 1.

Comparative Example 1

Comparative absorbent resin compositions (1)–(15) were obtained by mixing the water-absorbent resins A–H obtained in Referential Examples 1–8 at composition ratios indicated in Table 9 by following the procedure of Example 1.

TABLE 1

| Aperture of mesh | Water-absorbent resin A | Water-absorbent resin B | Water-absorbent resin C | Water-absorbent resin D | Water-absorbent resin E | Water-absorbent resin F | Water-absorbent resin G | Water-absorbent resin H |
|---|---|---|---|---|---|---|---|---|
| 850 μm on | 0.0 | 0.0 | 0.1 | 0.0 | 0.0 | 0.0 | 0.0 | 0.0 |
| 850 μm–500 μm | 43.2 | 9.3 | 2.3 | 0.3 | 1.6 | 0.8 | 0.0 | 0.0 |
| 500 μm–300 μm | 34.9 | 47.2 | 3.4 | 0.9 | 2.8 | 2.7 | 0.0 | 62.1 |
| 300 μm–150 μm | 17.5 | 37.1 | 8.6 | 82.7 | 85.1 | 85.2 | 0.0 | 31.1 |
| 150 μm–75 μm | 3.8 | 5.4 | 69.7 | 15.5 | 10.3 | 10.8 | 44.0 | 6.8 |
| 75 μm–45 μm | 0.5 | 0.7 | 11.2 | 0.6 | 0.2 | 0.5 | 46.0 | 0.0 |
| 45 μm pass | 0.2 | 0.3 | 4.7 | 0.0 | 0.0 | 0.0 | 10.0 | 0.0 |
| Average particle size (μm) | 456 | 317 | 105 | 185 | 201 | 198 | 71 | 300 |
| GV (g/g) | 28 | 32 | 29 | 28 | 42 | 45 | 26 | 41.3 |
| AAP (g/g) | 25 | 24 | 30 | 26 | 11 | 11 | 25 | 10 |
| SFC ($10^{-7}$ cm$^3$ × s × g$^{-1}$) | 45 | 3 | 50 | 57 | 0 | 0 | 0 | 0.3 |
| Soluble component (wt. %) | 10 | 13 | 10 | 15 | 25 | 13 | 10 | 13 |

TABLE 2

| Aperture of mesh | Water-absorbent resin comp. 1 | Water-absorbent resin comp. 2 | Water-absorbent resin comp. 3 | Water-absorbent resin comp. 4 | Water-absorbent resin comp. 5 | Water-absorbent resin comp. 6 |
|---|---|---|---|---|---|---|
| 850 μm on | 0.0 | 0.0 | 0.0 | 0.0 | 0.0 | 0.0 |
| 850 μm–500 μm | 14.6 | 22.8 | 30.9 | 13.2 | 21.7 | 30.3 |
| 500 μm–300 μm | 12.8 | 19.1 | 25.4 | 11.1 | 17.9 | 24.7 |
| 300 μm–150 μm | 11.3 | 13.0 | 14.8 | 63.1 | 50.1 | 37.1 |
| 150 μm–75 μm | 49.9 | 36.7 | 23.5 | 12.0 | 9.6 | 7.3 |
| 75 μm–45 μm | 8.0 | 5.9 | 3.7 | 0.6 | 0.6 | 0.5 |
| 45 μm pass | 3.4 | 2.5 | 1.7 | 0.0 | 0.1 | 0.1 |
| Average particle size (μm) | 131 | 169 | 339 | 231 | 266 | 332 |
| GV (g/g) | 28.7 | 28.5 | 28.3 | 28 | 28 | 28 |
| AAP (g/g) | 28.5 | 27.5 | 26.6 | 25.7 | 25.5 | 25.3 |
| SFC ($10^{-7}$ cm$^3$ × s × g$^{-1}$) | 51.1 | 56.6 | 57.1 | 52.2 | 57.6 | 60 |
| Soluble component (wt. %) | 10 | 10 | 10 | 13.5 | 12.5 | 11.5 |

TABLE 3

| Aperture of mesh | Water-absorbent resin comp. 7 | Water-absorbent resin comp. 8 | Water-absorbent resin comp. 9 | Water-absorbent resin comp. 10 | Water-absorbent resin comp. 11 |
|---|---|---|---|---|---|
| 850 μm on | 0.1 | 0.0 | 0.0 | 0.0 | 0.0 |
| 850 μm–500 μm | 4.4 | 5.8 | 7.2 | 39.0 | 30.7 |
| 500 μm–300 μm | 16.5 | 25.3 | 34.1 | 31.7 | 25.3 |
| 300 μm–150 μm | 17.1 | 22.9 | 28.6 | 24.3 | 37.8 |
| 150 μm–75 μm | 50.4 | 37.5 | 24.7 | 4.4 | 5.7 |
| 75 μm–45 μm | 8.1 | 6.0 | 3.9 | 0.5 | 0.4 |
| 45 μm pass | 3.4 | 2.5 | 1.5 | 0.2 | 0.1 |
| Average particle size (μm) | 130 | 169 | 244 | 420 | 337 |
| GV (g/g) | 29.9 | 30.5 | 31.1 | 29.4 | 32.2 |
| AAP (g/g) | 28.2 | 27 | 25.8 | 23.6 | 20.8 |
| SFC ($10^{-7}$ cm$^3$ × s × g$^{-1}$) | 54.2 | 23.5 | 13.4 | 24 | 23 |
| Soluble component (wt. %) | 10.9 | 11.5 | 12.1 | 11.5 | 14.5 |

TABLE 4

| Aperture of mesh | Comparative absorbent resin comp. 1 | Comparative absorbent resin comp. 2 | Comparative absorbent resin comp. 3 | Comparative absorbent resin comp. 4 | Comparative absorbent resin comp. 5 |
|---|---|---|---|---|---|
| 850 μm on | 0.0 | 0.0 | 0.0 | 0.1 | 0.0 |
| 850 μm–500 μm | 19.5 | 26.1 | 33.0 | 14.4 | 22.8 |
| 500 μm–300 μm | 43.5 | 41.1 | 38.6 | 13.7 | 19.9 |
| 300 μm–150 μm | 31.2 | 27.3 | 23.4 | 11.3 | 13.0 |
| 150 μm–75 μm | 4.9 | 4.6 | 4.2 | 49.7 | 36.6 |
| 75 μm–45 μm | 0.6 | 0.6 | 0.6 | 7.2 | 5.3 |
| 45 μm pass | 0.3 | 0.3 | 0.2 | 3.8 | 2.6 |
| Average particle size (μm) | 346 | 370 | 400 | 133 | 202 |
| GV (g/g) | 30.8 | 30 | 28.6 | 39.9 | 36.5 |
| AAP (g/g) | 24.3 | 24.5 | 24.7 | 15.2 | 18 |
| SFC ($10^{-7}$ cm$^3$ × s × g$^{-1}$) | 3 | 6 | 15.5 | 0 | 1.5 |
| Soluble component (wt. %) | 11.9 | 11.2 | 10.6 | 26.1 | 21.5 |

TABLE 5

| Aperture of mesh | Comparative absorbent resin comp. 6 | Comparative absorbent resin comp. 7 | Comparative absorbent resin comp. 8 | Comparative absorbent resin comp. 9 | Comparative absorbent resin comp. 10 |
|---|---|---|---|---|---|
| 850 μm on | 0.0 | 0.0 | 0.0 | 0.1 | 0.0 |
| 850 μm–500 μm | 30.9 | 13.0 | 21.6 | 30.2 | 22.4 |
| 500 μm–300 μm | 25.8 | 12.1 | 18.6 | 25.1 | 18.6 |
| 300 μm–150 μm | 14.8 | 5.2 | 8.7 | 12.2 | 51.3 |
| 150 μm–75 μm | 23.5 | 17.7 | 13.7 | 9.7 | 7.0 |
| 75 μm–45 μm | 3.4 | 44.0 | 31.6 | 19.1 | 0.4 |
| 45 μm pass | 1.6 | 8.0 | 5.8 | 3.6 | 0.1 |
| Average particle size (μm) | 341 | 74 | 142 | 334 | 273 |
| GV (g/g) | 33.1 | 26.6 | 27 | 27.4 | 35 |
| AAP (g/g) | 19.4 | 25 | 26 | 25 | 18.5 |
| SFC ($10^{-7}$ cm$^3$ × s × g$^{-1}$) | 4 | 0 | 2 | 5 | 0 |
| Soluble component (wt. %) | 16.9 | 10 | 10 | 10 | 17.5 |

TABLE 6

| Aperture of mesh | Comparative absorbent resin comp. 11 | Comparative Absorptive resin comp. 12 | Comparative Absorptive resin comp. 13 | Comparative Absorptive resin comp. 14 | Comparative Absorptive resin comp. 15 |
|---|---|---|---|---|---|
| 850 μm on | 0.0 | 0.0 | 0.1 | 0.1 | 0.0 |
| 850 μm–500 μm | 14.1 | 0.9 | 1.3 | 1.7 | 0.2 |
| 500 μm–300 μm | 12.4 | 1.6 | 2.1 | 2.6 | 31.5 |
| 300 μm–150 μm | 64.8 | 60.5 | 45.6 | 30.8 | 56.9 |
| 150 μm–75 μm | 8.3 | 31.8 | 42.6 | 53.4 | 11.1 |
| 75 μm–45 μm | 0.3 | 3.8 | 5.9 | 8.0 | 0.3 |
| 45 μm pass | 0.1 | 1.4 | 2.4 | 3.3 | 0.0 |
| Average particle size (μm) | 241 | 186 | 148 | 127 | 247 |
| GV (g/g) | 37.8 | 28.7 | 28.5 | 28.3 | 35 |
| AAP (g/g) | 15.2 | 28.8 | 28 | 27.2 | 18 |
| SFC ($10^{-7}$ cm$^3$ × s × g$^{-1}$) | 0 | 61 | 40 | 44 | 0.5 |
| Soluble component (wt. %) | 20.5 | 11.5 | 12.5 | 13.5 | 14 |

TABLE 7

|  | Bulk specific gravity (g/ml) |
|---|---|
| Water-absorbent resin A | 0.67 |
| Water-absorbent resin B | 0.7 |
| Water-absorbent resin C | 0.92 |
| Water-absorbent resin D | 0.94 |
| Water-absorbent resin E | 0.94 |
| Water-absorbent resin F | 0.93 |
| Water-absorbent resin G | 0.84 |
| Water-absorbent resin H | 0.85 |

TABLE 8

|  | Composition ratio of water-absorbent resin A to E | Bulk specific gravity (g/ml) |
|---|---|---|
| Water-absorbent resin comp. 1 | A:C = 30:70 | 0.92 |
| Water-absorbent resin comp. 2 | A:C = 50:50 | 0.9 |
| Water-absorbent resin comp. 3 | A:C = 70:30 | 0.86 |
| Water-absorbent resin comp. 4 | A:D = 30:70 | 0.92 |
| Water-absorbent resin comp. 5 | A:D = 50:50 | 0.9 |
| Water-absorbent resin comp. 6 | A:D = 30:70 | 0.86 |
| Water-absorbent resin comp. 7 | B:C = 30:70 | 0.91 |
| Water-absorbent resin comp. 8 | B:C = 50:50 | 0.9 |
| Water-absorbent resin comp. 9 | B:C = 70:30 | 0.83 |
| Water-absorbent resin comp. 10 | A:E = 90:10 | 0.84 |
| Water-absorbent resin comp. 11 | A:E = 70:30 | 0.81 |

TABLE 9

| | Composition ratio of water-absorbent resins A to H | Bulk specific density (g/ml) |
|---|---|---|
| Comparative absorbent resin comp. 1 | A:B = 30:70 | 0.69 |
| Comparative absorbent resin comp. 2 | A:B = 50:50 | 0.68 |
| Comparative absorbent resin comp. 3 | A:B = 70:30 | 0.67 |
| Comparative absorbent resin comp. 4 | A:F = 30:70 | 0.97 |
| Comparative absorbent resin comp. 5 | A:F = 50:50 | 0.94 |
| Comparative absorbent resin comp. 6 | A:F = 70:30 | 0.86 |
| Comparative absorbent resin comp. 7 | A:G = 30:70 | 0.73 |
| Comparative absorbent resin comp. 8 | A:G = 50:50 | 0.72 |
| Comparative absorbent resin comp. 9 | A:G = 70:30 | 0.67 |
| Comparative absorbent resin comp. 10 | A:E = 50:50 | 0.94 |
| Comparative absorbent resin comp. 11 | A:E = 30:70 | 0.97 |
| Comparative absorbent resin comp. 12 | C:D = 30:70 | 0.93 |
| Comparative absorbent resin comp. 13 | C:D = 50:50 | 0.93 |
| Comparative absorbent resin comp. 14 | C:D = 70:30 | 0.93 |
| Comparative absorbent resin comp. 15 | H:D = 50:50 | 0.90 |

TABLE 10

| | CSF (g/g) |
|---|---|
| Water-absorbent resin A | 23 |
| Water-absorbent resin B | 28 |
| Water-absorbent resin C | 30 |
| Water-absorbent resin D | 30 |
| Water-absorbent resin E | 31 |
| Water-absorbent resin F | 33 |
| Water-absorbent resin G | 24 |
| Water-absorbent resin H | 11.8 |

TABLE 11

| | Composition ratio | CSF (g/g) | Index of increase of capillary suction force |
|---|---|---|---|
| Water-absorbent resin composition 1 | A:C = 30:70 | 29.9 | 1.10 |
| Water-absorbent resin composition 2 | A:C = 50:50 | 30.1 | 1.14 |
| Water-absorbent resin composition 3 | A:C = 70:30 | 28.7 | 1.20 |
| Water-absorbent resin composition 4 | A:D = 30:70 | 30.1 | 1.10 |
| Water-absorbent resin composition 5 | A:D = 50:50 | 28.9 | 1.10 |
| Water-absorbent resin composition 6 | A:D = 30:70 | 26.8 | 1.10 |
| Water-absorbent resin composition 7 | B:C = 30:70 | 32 | 1.10 |
| Water-absorbent resin composition 8 | B:C = 50:50 | 31.4 | 1.10 |
| Water-absorbent resin composition 9 | B:C = 70:30 | 33 | 1.15 |
| Water-absorbent resin composition 10 | A:E = 90:10 | 30 | 1.26 |
| Water-absorbent resin composition 11 | A:E = 70:30 | 30 | 1.19 |

TABLE 12

| | Composition ratio | CSF (g/g) | Index of increase of capillary suction force |
|---|---|---|---|
| Comparative absorbent resin composition 1 | A:B = 30:70 | 26.2 | 0.99 |
| Comparative absorbent resin composition 2 | A:B = 50:50 | 24.7 | 0.97 |
| Comparative absorbent resin composition 3 | A:B = 70:30 | 23 | 0.94 |
| Comparative absorbent resin composition 4 | A:F = 30:70 | 30.7 | 1.02 |
| Comparative absorbent resin composition 5 | A:F = 50:50 | 28.4 | 1.01 |
| Comparative absorbent resin composition 6 | A:F = 70:30 | 25.5 | 0.98 |
| Comparative absorbent resin composition 7 | A:G = 30:70 | 5.6 | 0.24 |
| Comparative absorbent resin composition 8 | A:G = 50:50 | 5.7 | 0.24 |
| Comparative absorbent resin composition 9 | A:G = 70:30 | 4.2 | 0.18 |
| Comparative absorbent resin composition 12 | C:D = 30:70 | 30 | 1.00 |
| Comparative absorbent resin composition 13 | C:D = 50:50 | 30 | 1.00 |
| Comparative absorbent resin composition 14 | C:D = 70:30 | 30 | 1.00 |
| Comparative absorbent resin composition 15 | H:D = 50:50 | 15.1 | 0.72 |

TABLE 13

| | Amount of rewet (g) |
|---|---|
| Water-absorbent resin A | 0.53 |
| Water-absorbent resin B | 0.47 |
| Water-absorbent resin C | 0.59 |
| Water-absorbent resin D | 0.6 |
| Water-absorbent resin E | 0.51 |
| Water-absorbent resin F | 0.6 |
| Water-absorbent resin G | 0.48 |
| Water-absorbent resin H | 0.6 |

TABLE 14

| | Amount of rewet (g) |
|---|---|
| Water-absorbent resin composition 1 | 0.31 |
| Water-absorbent resin composition 2 | 0.32 |
| Water-absorbent resin composition 3 | 0.34 |
| Water-absorbent resin composition 4 | 0.31 |
| Water-absorbent resin composition 5 | 0.36 |
| Water-absorbent resin composition 6 | 0.35 |
| Water-absorbent resin composition 7 | 0.3 |
| Water-absorbent resin composition 8 | 0.29 |
| Water-absorbent resin composition 9 | 0.31 |
| Water-absorbent resin composition 10 | 0.36 |
| Water-absorbent resin composition 11 | 0.35 |

TABLE 15

| | Amount of rewet (g) |
|---|---|
| Comparative absorbent resin composition 1 | 0.61 |
| Comparative absorbent resin composition 2 | 0.6 |
| Comparative absorbent resin composition 3 | 0.6 |
| Comparative absorbent resin composition 4 | 0.7 |
| Comparative absorbent resin composition 5 | 0.64 |

TABLE 15-continued

| | Amount of rewet (g) |
|---|---|
| Comparative absorbent resin composition 6 | 0.71 |
| Comparative absorbent resin composition 7 | 0.51 |
| Comparative absorbent resin composition 8 | 0.55 |
| Comparative absorbent resin composition 9 | 0.54 |
| Comparative absorbent resin composition 10 | 0.49 |
| Comparative absorbent resin composition 11 | 0.45 |
| Comparative absorbent resin composition 12 | 0.45 |
| Comparative absorbent resin composition 13 | 0.42 |
| Comparative absorbent resin composition 14 | 0.43 |
| Comparative absorbent resin composition 15 | 0.60 |

(Results)

The water-absorbent resin compositions 1–3 are mixtures formed of water-absorbent resins A and C at varying mixing ratios, the water-absorbent resin compositions 4–6 are mixtures formed of water-absorbent resins A and D at varying mixing ratios, the water-absorbent resin compositions 7–9 are mixtures formed of water-absorbent resins B and C at varying mixing ratios, and the water-absorbent resin compositions 10 and 11 are mixtures formed of A and E at varying mixing ratios. The water-absorbent resin compositions of this invention, as shown in FIG. 3, have their bulk specific gravities increased owing to of the mixture of water-absorbent resins and brought to such bulk specific gravities as surpass the bulk specific densities attained by the addition of corresponding raw material resins.

Figure 4:
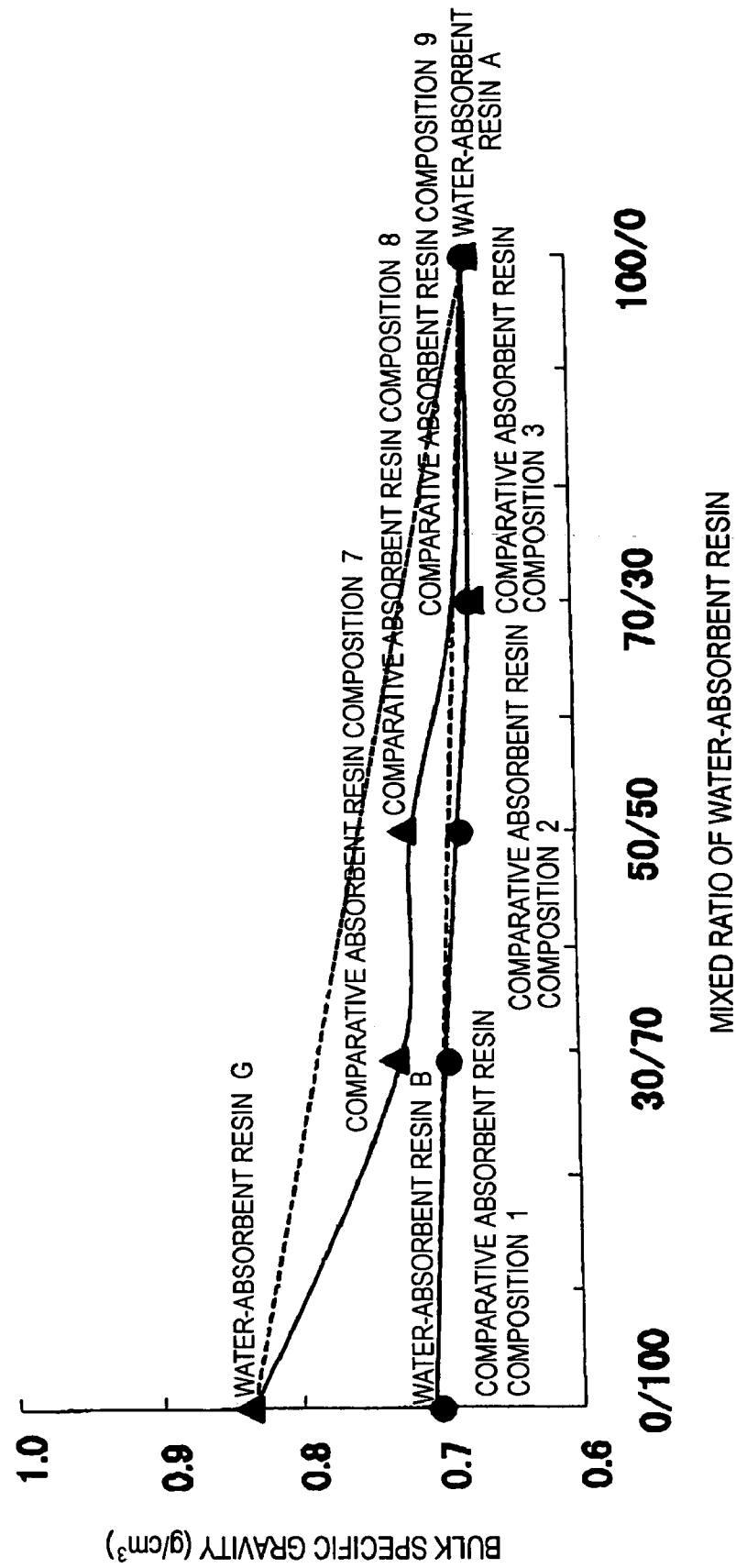
FIG. 4 is a diagram illustrating the difference in bulk specific density due to the difference in the combining ratio of the component water-absorbent resins.
Figure 5:
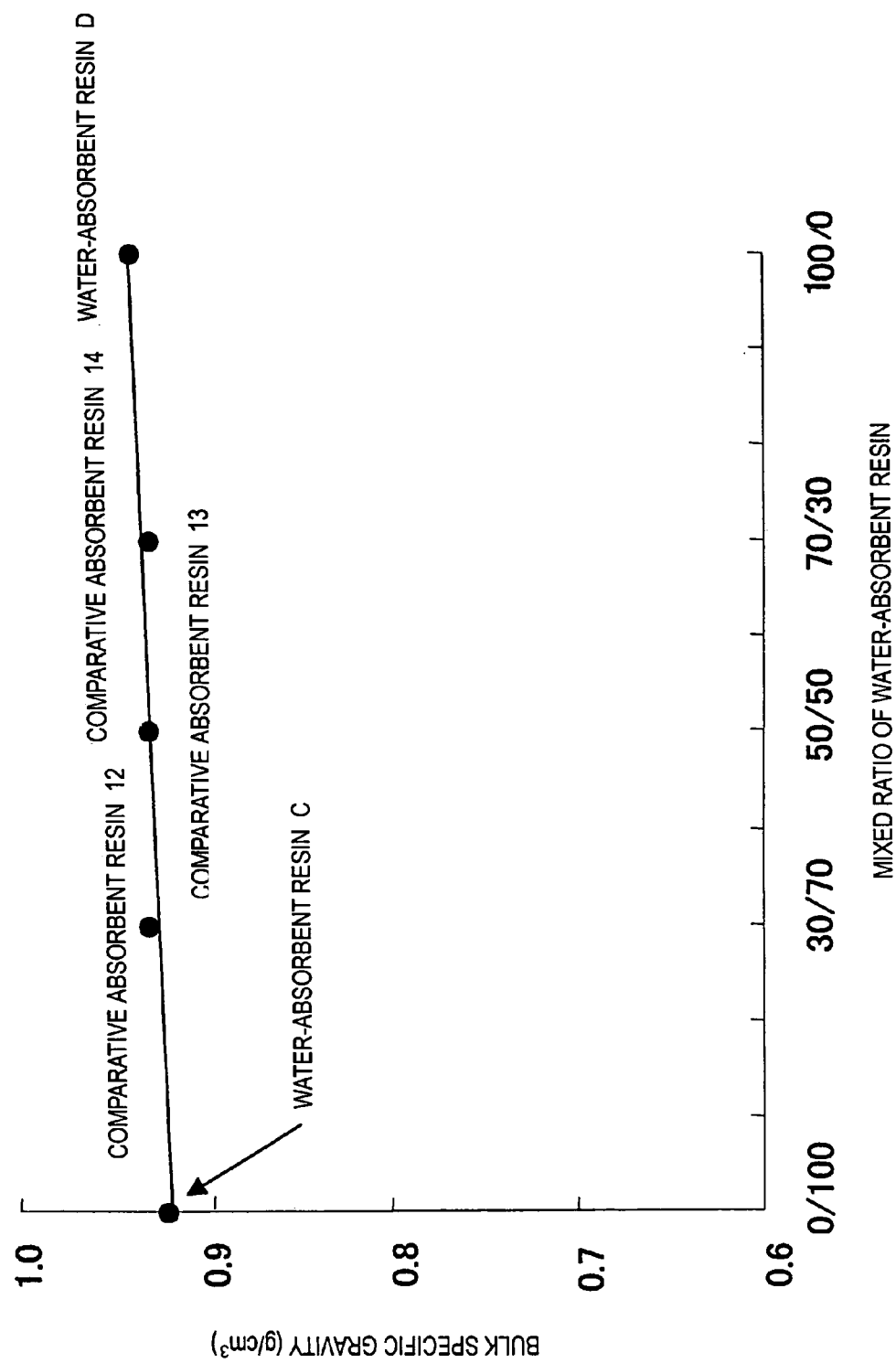
FIG. 5 is a diagram illustrating the difference in bulk specific density due to the difference in the combining ratio of the component water-absorbent resins.

The comparative absorbent resin compositions 1–3 are mixtures formed of water-absorbent resins A and B at varying mixing ratios, the comparative absorbent resin compositions 4–6 are mixtures formed of water-absorbent resins A and F at varying mixing ratios, and the comparative absorbent resin compositions 7–9 are mixtures formed of water-absorbent resins A and G at varying mixing ratios. As shown in FIG. 4, the bulk specific gravities of the resin compositions formed by mixing water-absorbent resins A and B do not surpass the bulk specific gravities attained by arithmetic addition of corresponding raw material resin at any of the composition ratios.

The comparative absorbent resin compositions 12–14 are mixtures formed of water-absorbent resins C and D, i.e. the products of suspension polymerization, at varying mixing ratios. The bulk specific gravities of the mixtures formed exclusively of the water-absorbent resins resulting from suspension polymerization are not observed to surpass the additive bulk specific gravities of corresponding raw material resins.

Figure 3:
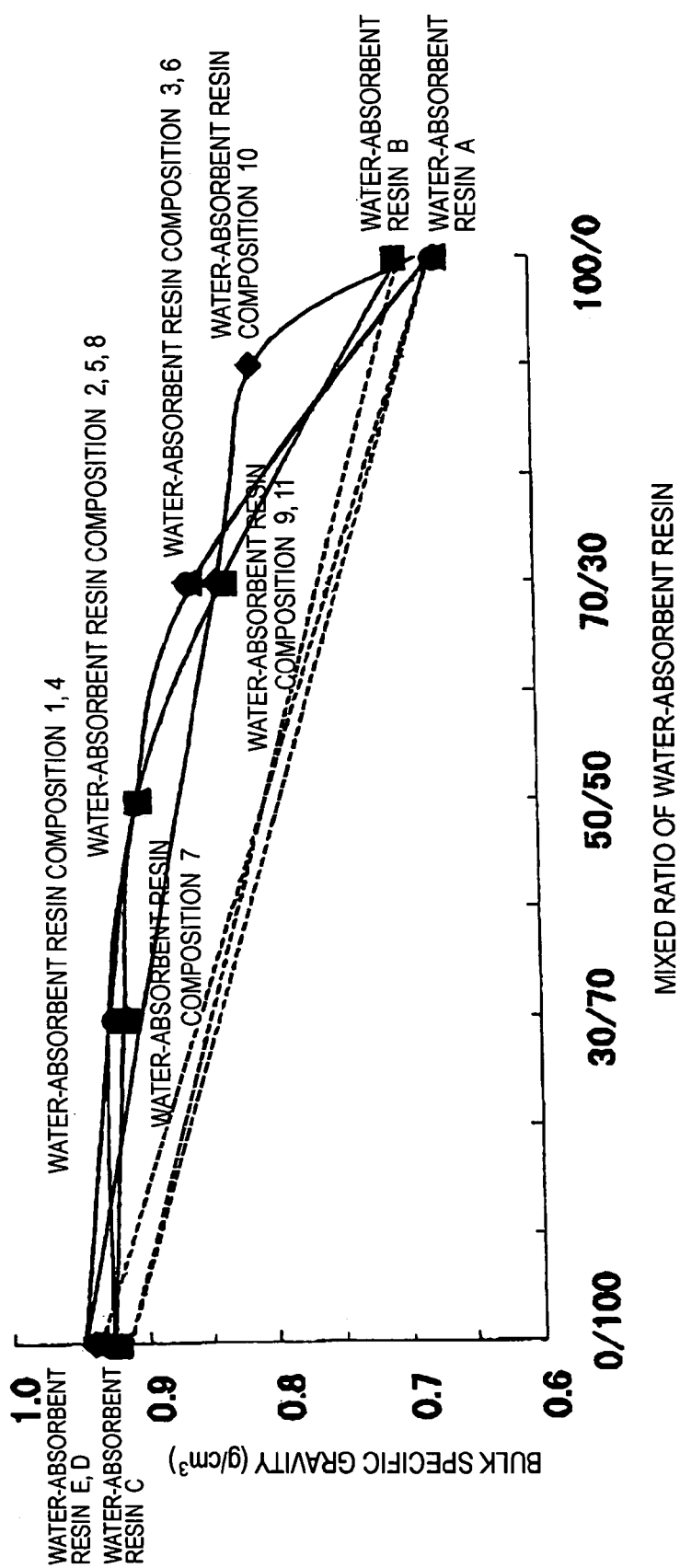
FIG. 3 is a diagram illustrating the difference in bulk specific density due to the difference in the combining ratio of the component water-absorbent resins.
Figure 6:
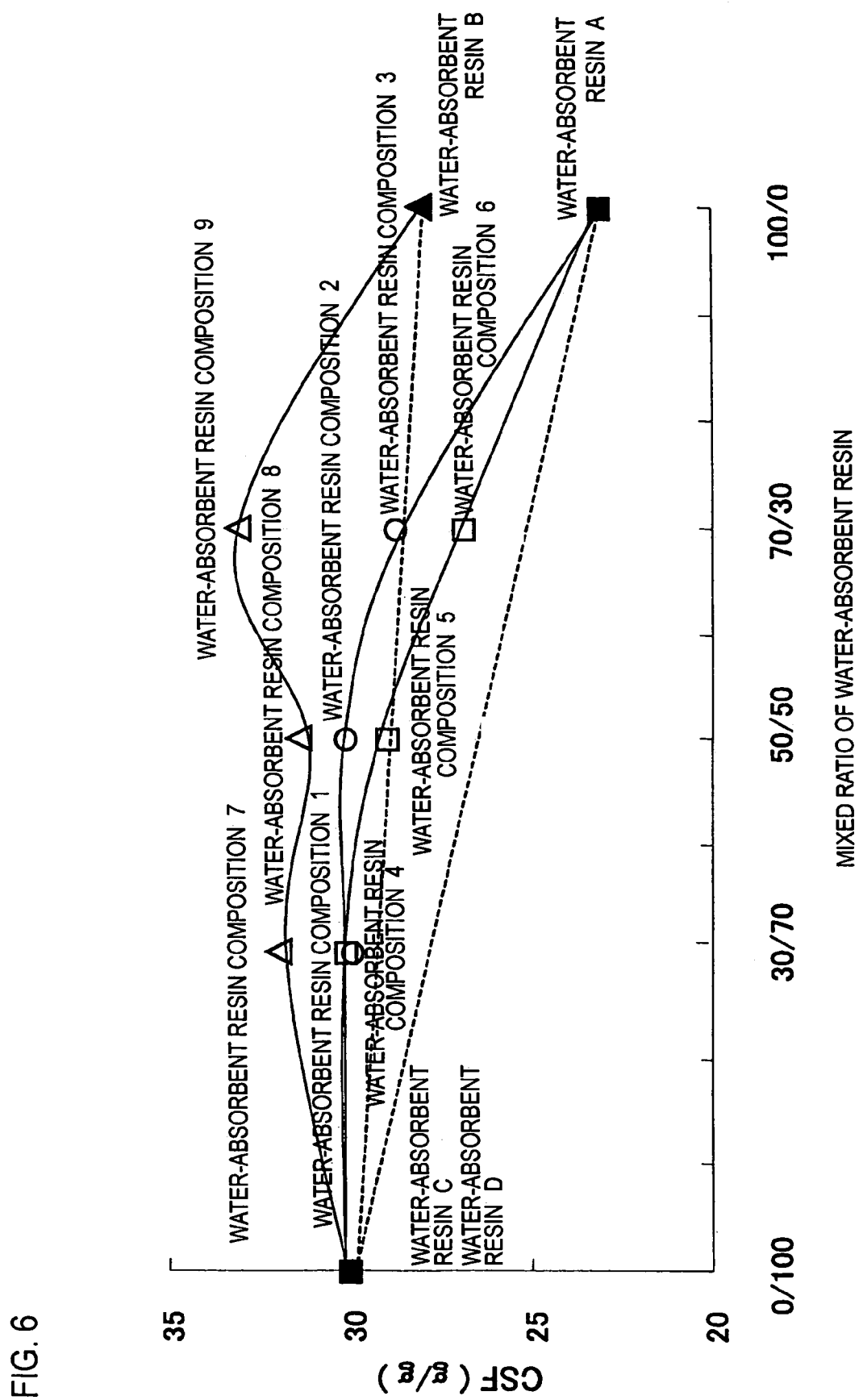
FIG. 6 is a diagram illustrating the difference in CSF due to the difference in the combining ratio of the component water-absorbent resins.

FIG. 6 is a diagram showing the capillary absorption ratios (CSF) relative to mixing ratios with respect to the resin compositions having the bulk specific gravities thereof compared in FIG. 3. Similarly to the bulk specific gravities, the raw material resins are observed to increase the magnitudes of CSF synergistically in the resin compositions.

Figure 7:
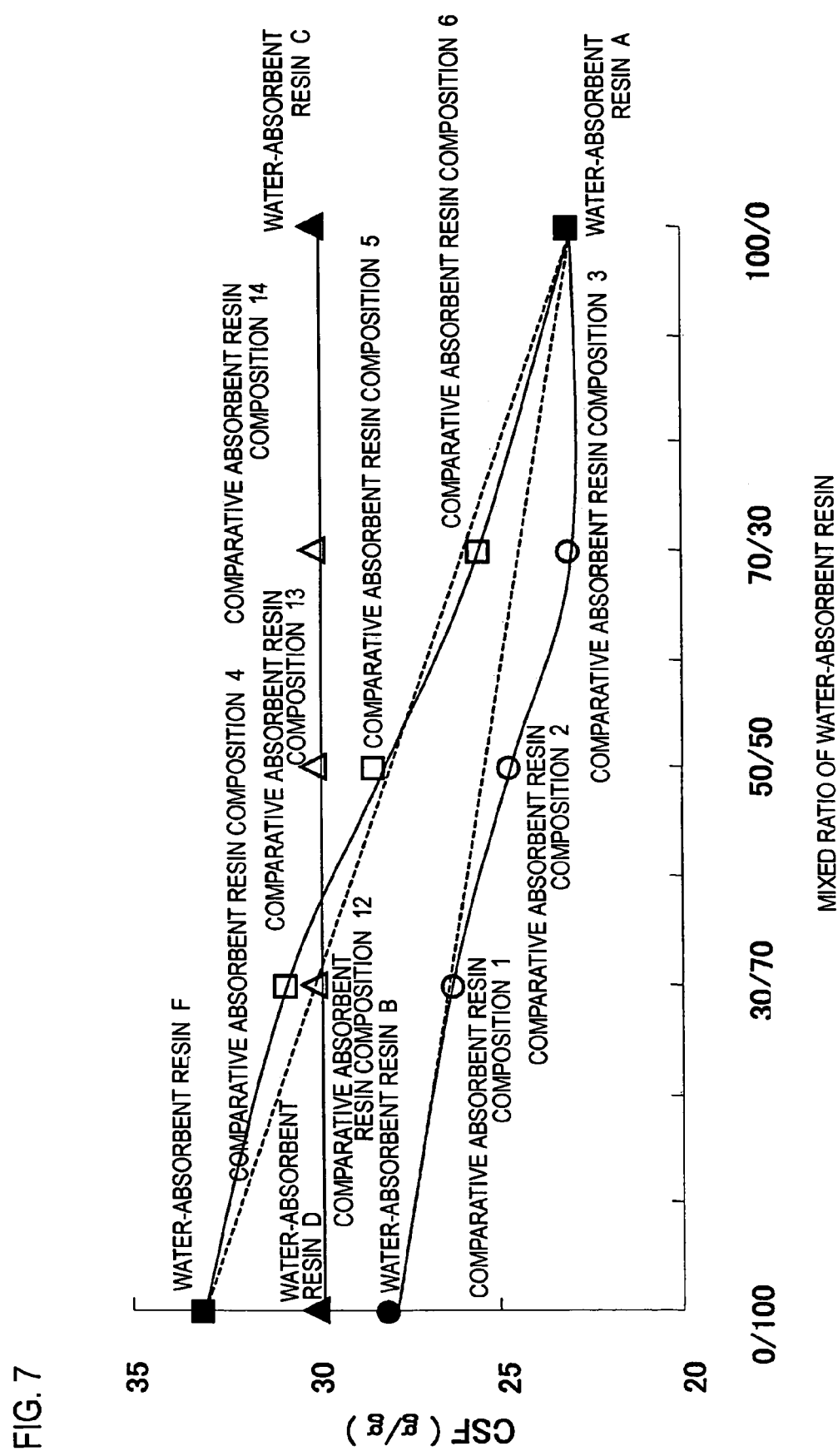
FIG. 7 is a diagram illustrating the difference in CSF due to the difference in the combining ratio of the component water-absorbent resins.

FIG. 7 is a diagram showing the CSF relative to mixing ratios with respect to the comparative absorbent resin compositions 1–6 and 10–14. The raw material resins are not observed to increase the magnitudes of CSF synergistically in the resin compositions.

Figure 8:
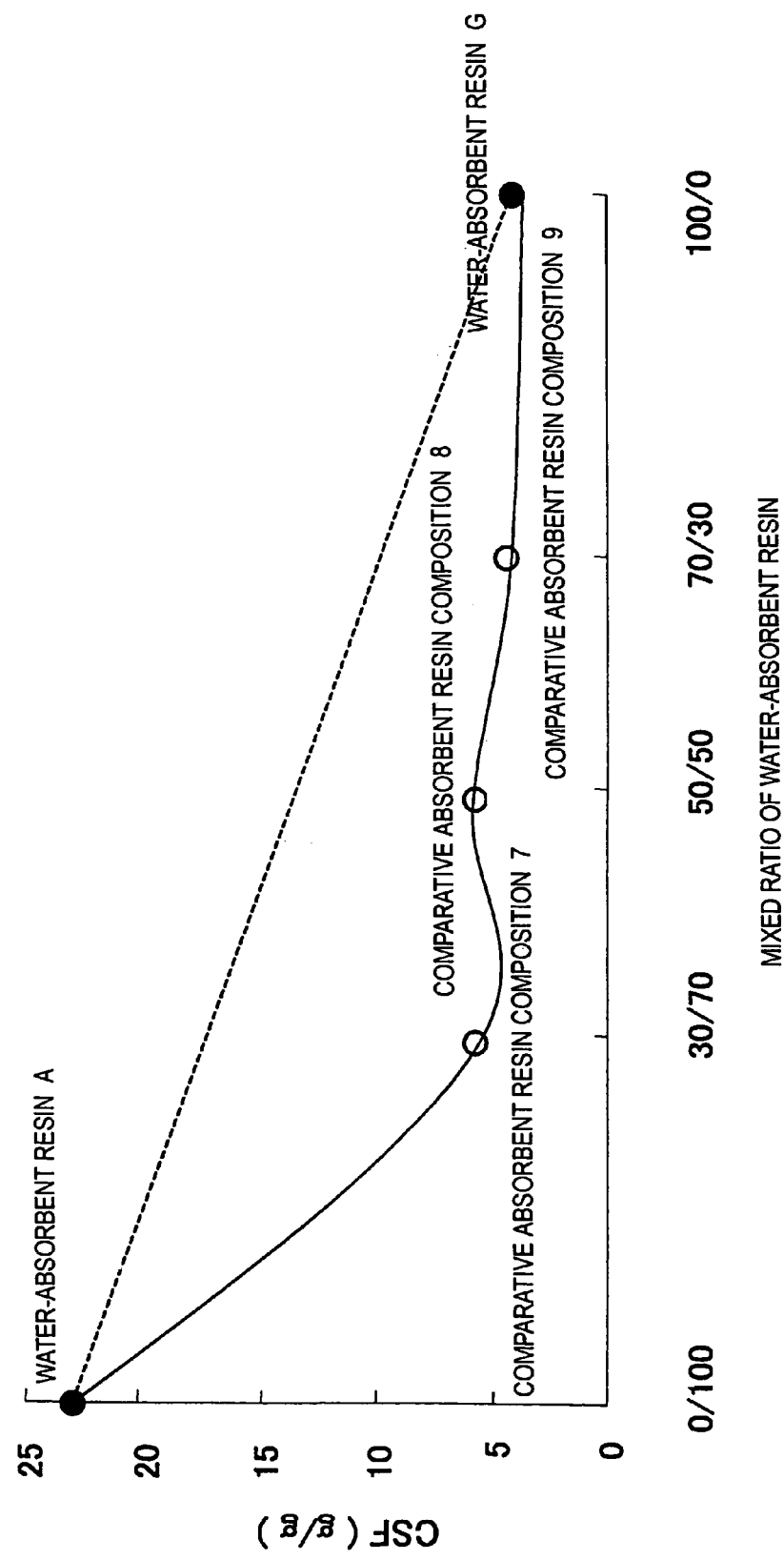
FIG. 8 is a diagram illustrating the difference in CSF due to the difference in the combining ratio of the component water-absorbent resins.

FIG. 8 is a diagram showing the CSF relative to the mixing ratios with respect to the, comparative absorbent resin compositions 7–9. The magnitudes of CSF of these resin compositions fall far below the magnitudes of CSF produced synergistically by corresponding raw material resins.

Figure 9:
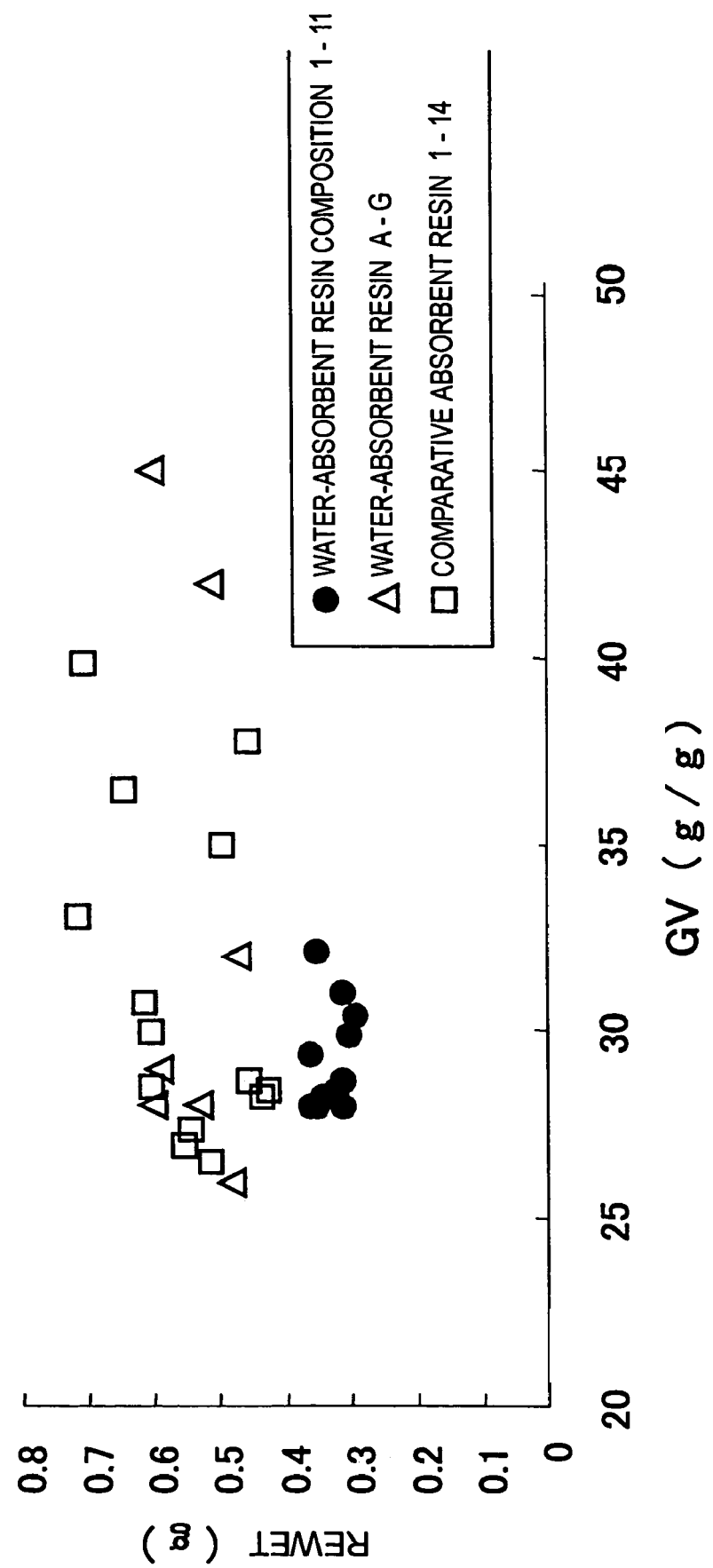
FIG. 9 is a diagram illustrating the difference in the amount of rewet due to the difference in the combining ratio of the component water-absorbent resins.

The relation between the absorption capacity under no pressure and the amount of rewet obtained of the water-absorbent resin compositions 1–11 and the comparative absorbent resins 1–14 are shown in FIG. 9. It is clear from the diagram that the water-absorbent resin compositions of this invention invariably have smaller amounts of rewet than any of the raw material resins A–G.

Figure 10:
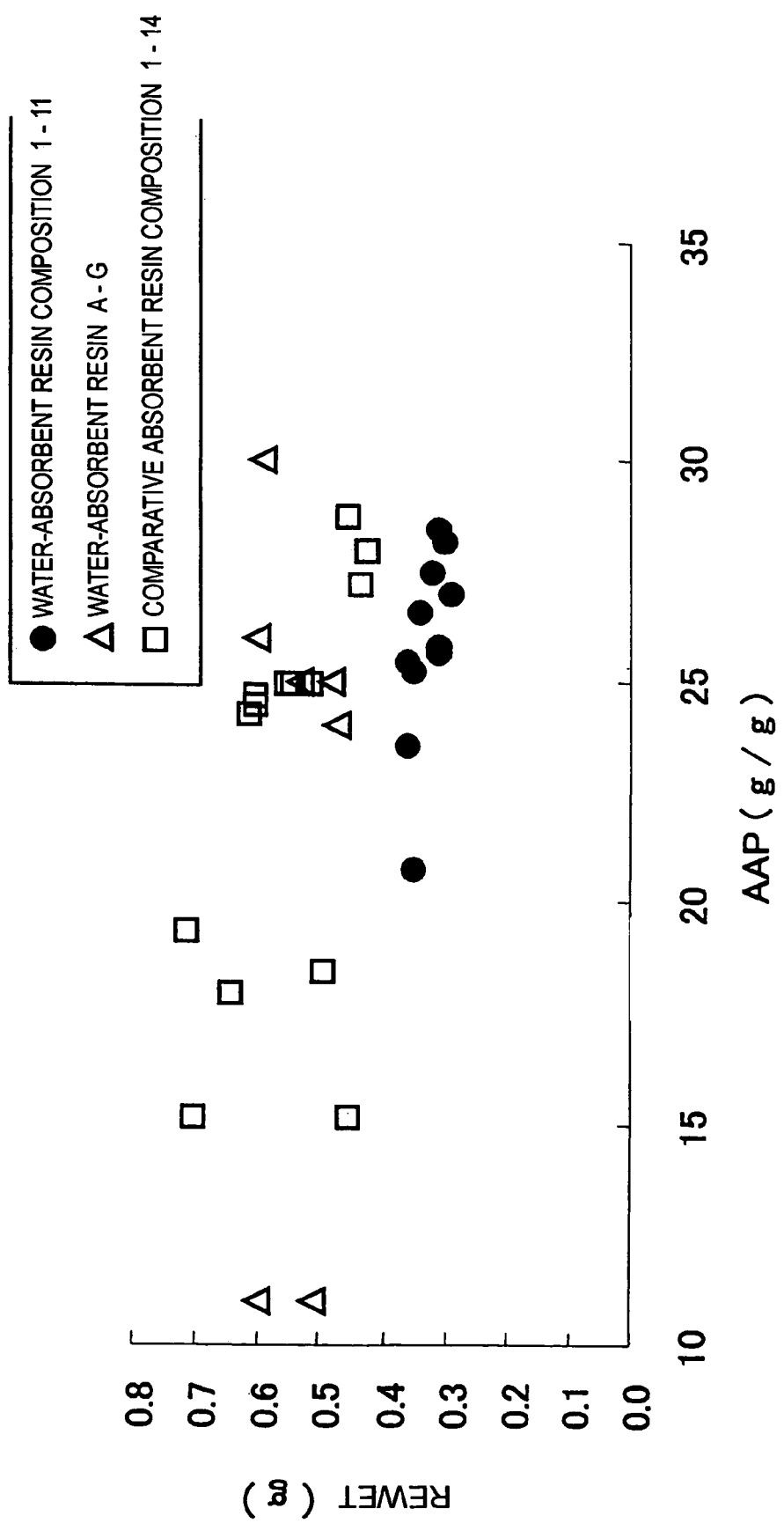
FIG. 10 is a diagram illustrating the difference in the amount of rewet due to the difference in the combining ratio of the component water-absorbent resins.

The relation between the absorption capacity under pressure and the amount of rewet obtained of the water-absorbent resin compositions 1–11 and the comparative absorbent resins 1–14 is shown in FIG. 10. The water-absorbent resin compositions of this invention, owing to the fact that the absorption capacity under pressure exceed 20 g/g, are enabled to decrease their amounts of rewet more than any of the raw material resins A-G.

The invention claimed is:

1. A water-absorbent resin composition, comprising a water-absorbent resin (R1) obtained by aqueous solution polymerization and a water-absorbent resin (R2) obtained by reversed-phase suspension polymerization or reversed-phase emulsion polymerization and satisfying any of the following conditions (a)–(c),
   (a) that a capillary suction force capacity of a 0.9 wt. % physiological saline in the gradient of negative pressure of 20 cm be not less than 20 g/g,
   (b) that an absorption capacity under pressure of a 0.9 wt. % physiological saline under be 4.83 kPa at 60 mm. be not less than 20 g/g, and
   (c) that a flow conductivity of a 0.69 wt. % physiological saline be not less than 10 (unit: $10^{-7} \times cm^3 \times s \times g^{-1}$);
   wherein the water-absorbent resin (R1) is obtained by aqueous solution polymerization of polymerizable monomers comprising 70–100% of acrylic acid and/or salts thereof and the water-absorbent resin (R2) obtained by reversed-phase suspension polymerization or reversed-phase emulsion polymerization of polymerizable monomers comprising 70–100 mol % of acrylic acid and/or salts thereof.

2. A water-absorbent resin composition according to claim 1 wherein said water-absorbent resin composition satisfies the conditions of (a) and (b) or the conditions of (a) and (c).

3. A water-absorbent resin composition according to claim 1 wherein said water-absorbent resin composition satisfies all the conditions of (a), (b), and (c).

4. A water-absorbent resin composition according to claim 1 wherein said water-absorbent resin composition have a weight average particle size in the range of 100–600 μm.

5. A water-absorbent resin composition according to claim 1 wherein a particle having a particle size of 850 μm–75 μm is comprised in the range of not less than 85 wt. % and a particle having a particle size smaller than 45 μm is comprised in the range of not more than 5 wt. %.

6. A water-absorbent resin composition according to claim 1 wherein the soluble component not more than 20 wt. % of the water-absorbent resin composition.

7. A method for the production of a water-absorbent resin composition set forth in claim 1, which comprises blending a water-absorbent resin (R1) (R2) to dry mix batchwise or continuously at a weight ratio R1/R2 in the range of 1/9–9/1, in an atmosphere having a relative humidity of not more than 40% RH.

8. A water absorbent article comprising the water-absorbent resin composition set forth in claim 1.

9. A water-absorbent resin composition according to claim 2, wherein the soluble component not more than 20 wt. % of the water-absorbent resin composition.

10. A water-absorbent resin composition according to claim 3, wherein the soluble component not more than 20 wt. % of the water-absorbent resin composition.

11. A water-absorbent resin composition according to claim 4, wherein the soluble component not more than 20 wt. % of the water-absorbent resin composition.

12. A water-absorbent resin composition according to claim 5, wherein the soluble component not more than 20 wt. % of the water-absorbent resin composition.

13. A method for the production of a water-absorbent resin composition set forth in claim 2, which comprises blending a water-absorbent resin (R1) (R2) to dry mix batchwise or continuously at a weight ratio R1/R2 in the range of 1/9–9/1, in an atmosphere having a relative humidity of not more than 40% RH.

14. A method for the production of a water-absorbent resin composition set forth in claim 3, which comprises blending a water-absorbent resin (R1) (R2) to dry mix batchwise or continuously at a weight ratio R1/R2 in the range of 1/9–9/1, in an atmosphere having a relative humidity of not more than 40% RH.

15. A method for the production of a water-absorbent resin composition set forth in claim 4, which comprises blending a water-absorbent resin (R1) (R2) to dry mix batchwise or continuously at a weight ratio R1/R2 in the range of 1/9–9/1, in an atmosphere having a relative humidity of not more than 40% RH.

16. A method for the production of a water-absorbent resin composition set forth in claim 5, which comprises blending a water-absorbent resin (R1) (R2) to dry mix batchwise or continuously at a weight ratio R1/R2 in the range of 1/9–9/1, in an atmosphere having a relative humidity of not more than 40% RH.

17. A method for the production of a water-absorbent resin composition set forth in claim 6, which comprises blending a water-absorbent resin (R1) (R2) to dry mix batchwise or continuously at a weight ratio R1/R2 in the range of 1/9–9/1, in an atmosphere having a relative humidity of not more than 40% RH.

18. A method for the production of a water-absorbent resin composition set forth in claim 9, which comprises blending a water-absorbent resin (R1) (R2) to dry mix batchwise or continuously at a weight ratio R1/R2 in the range of 1/9–9/1, in an atmosphere having a relative humidity of not more than 40% RH.

19. A method for the production of a water-absorbent resin composition set forth in claim 10, which comprises blending a water-absorbent resin (R1) (R2) to dry mix batchwise or continuously at a weight ratio R1/R2 in the range of 1/9–9/1, in an atmosphere having a relative humidity of not more than 40% RH.

20. A method for the production of a water-absorbent resin composition set forth in claim 11, which comprises blending a water-absorbent resin (R1) (R2) to dry mix batchwise or continuously at a weight ratio R1/R2 in the range of 1/9–9/1, in an atmosphere having a relative humidity of not more than 40% RH.

21. A method for the production of a water-absorbent resin composition set forth in claim 12, which comprises blending a water-absorbent resin (R1) (R2) to dry mix batchwise or continuously at a weight ratio R1/R2 in the range of 1/9–9/1, in an atmosphere having a relative humidity of not more than 40% RH.

22. A water absorbent article comprising the water-absorbent resin composition set forth in claim 2.

23. A water absorbent article comprising the water-absorbent resin composition set forth in claim 3.

24. A water absorbent article comprising the water-absorbent resin composition set forth in claim 4.

25. A water absorbent article comprising the water-absorbent resin composition set forth in claim 5.

26. A water absorbent article comprising the water-absorbent resin composition set forth in claim 6.

27. A water absorbent article comprising the water-absorbent resin composition set forth in claim 9.

28. A water absorbent article comprising the water-absorbent resin composition set forth in claim 10.

29. A water absorbent article comprising the water-absorbent resin composition set forth in claim 11.

30. A water absorbent article comprising the water-absorbent resin composition set forth in claim 12.

* * * * *